United States Patent [19]

Russell et al.

[11] Patent Number: 5,231,005
[45] Date of Patent: Jul. 27, 1993

[54] METHOD AND APPARATUS FOR SCREENING CELLS OR FORMED BODIES WITH POPULATIONS EXPRESSING SELECTED CHARACTERISTICS

[75] Inventors: Thomas Russell, Miami; Kenneth H. Kortright, Davie; Wallace H. Coulter, Miami Springs; Carlos M. Rodriguez, Miami; Ronald Paul, North Miami Beach; Constance M. Hajek; James C. Hudson, both of Miami, all of Fla.

[73] Assignee: Coulter Corporation, Hialeah, Fla.

[21] Appl. No.: 849,481

[22] Filed: Mar. 10, 1992

Related U.S. Application Data

[63] Continuation of Ser. No. 285,856, Dec. 16, 1988, abandoned, Continuation-in-part of Ser. No. 25,345, Mar. 13, 1987, abandoned.

[51] Int. Cl.⁵ ............... C12Q 1/00; C12Q 1/06; C12N 1/00
[52] U.S. Cl. .................... 435/7.21; 435/7.24; 435/39; 435/243; 435/11; 435/12; 436/10; 436/52; 436/148; 436/149; 436/173; 356/336; 356/335; 356/39; 250/461.2
[58] Field of Search ............ 356/336, 335, 39; 250/461.2; 377/11, 12; 435/7.21, 30, 34, 7.24, 39, 243; 436/10, 52, 148, 149, 173

[56] References Cited

U.S. PATENT DOCUMENTS

| | | | |
|---|---|---|---|
| 4,219,411 | 8/1980 | Yen | 250/461.2 |
| 4,452,773 | 6/1984 | Molday | 436/526 |
| 4,599,307 | 7/1986 | Saunders | 435/34 |
| 4,747,685 | 5/1988 | Suzuki | 356/36 |

OTHER PUBLICATIONS

Leif, et al., "Development of Instrumentation ..."; pp. 1492-1498, Clin Chem. vol. 23, No. 8, 1977.

Primary Examiner—John W. Rollins
Attorney, Agent, or Firm—Foley & Lardner

[57] ABSTRACT

A method and apparatus for automatically and rapidly, retrieving, counting and/or analyzing at least one selected population of cells or formed bodies, such as a white blood cell population and at least one subset thereof of a whole blood sample or portion thereof. A volume of a biological medium containing the white blood cells is prepared and at least one reactant specific or preferential at least to some selected biological cells is introduced thereto and rapidly mixed for a short period of time. The opacity and/or volume parameter of the cells can be modified and the mixture is then counted and analyzed in one or more steps to obtain the desired white blood cell population and subset analysis. The biological sample can be a whole blood sample and the reactant can include or be a lyse or a monoclonal antibody bound to microspheres, which will bind to specific ones of the cells or a combination of lyse and microspheres with antibody bound thereto. The microspheres can be magnetic and the bound cells can be magnetically removed for retrieving and analyzing the remaining blood cell population.

160 Claims, 20 Drawing Sheets

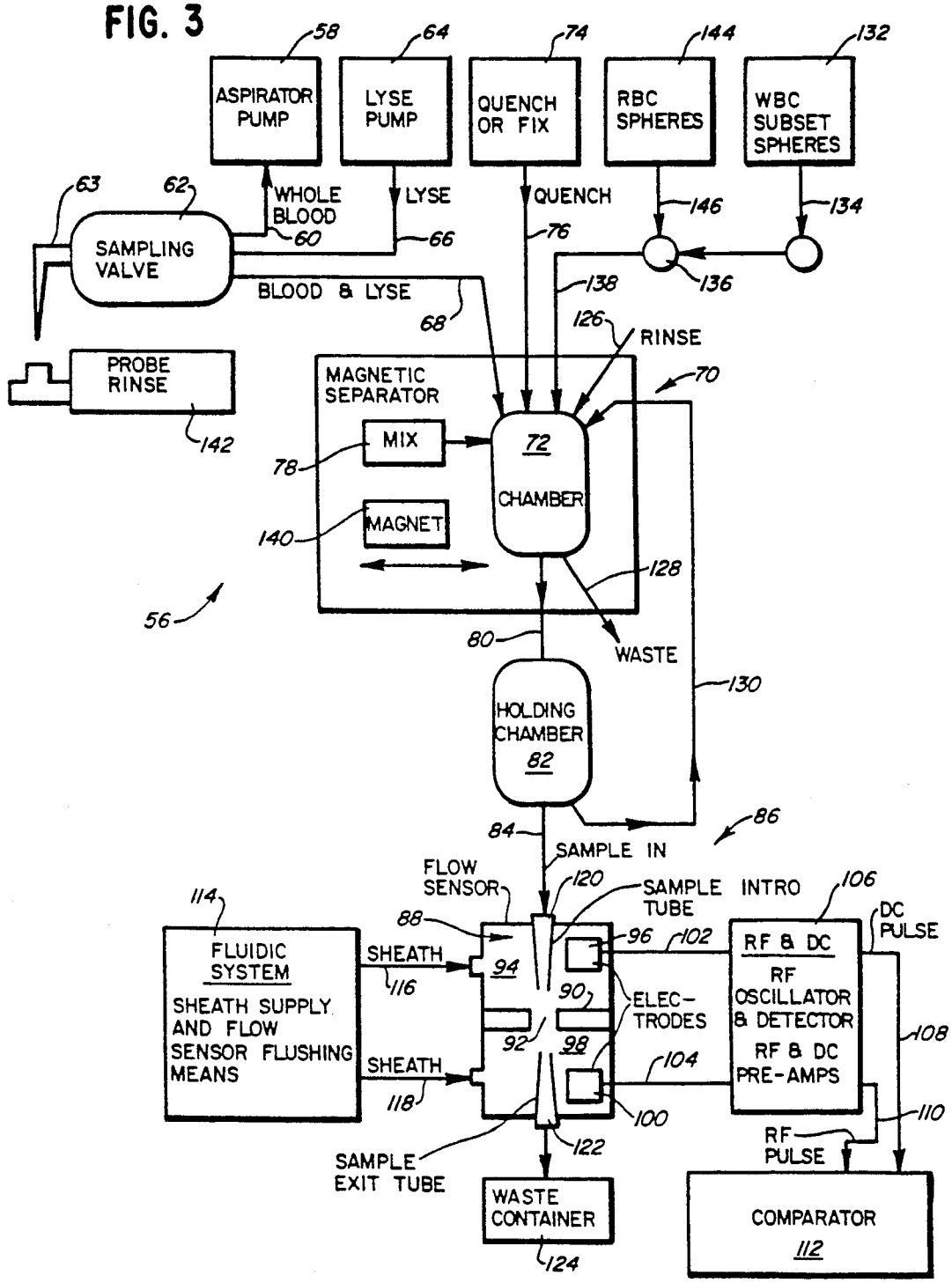

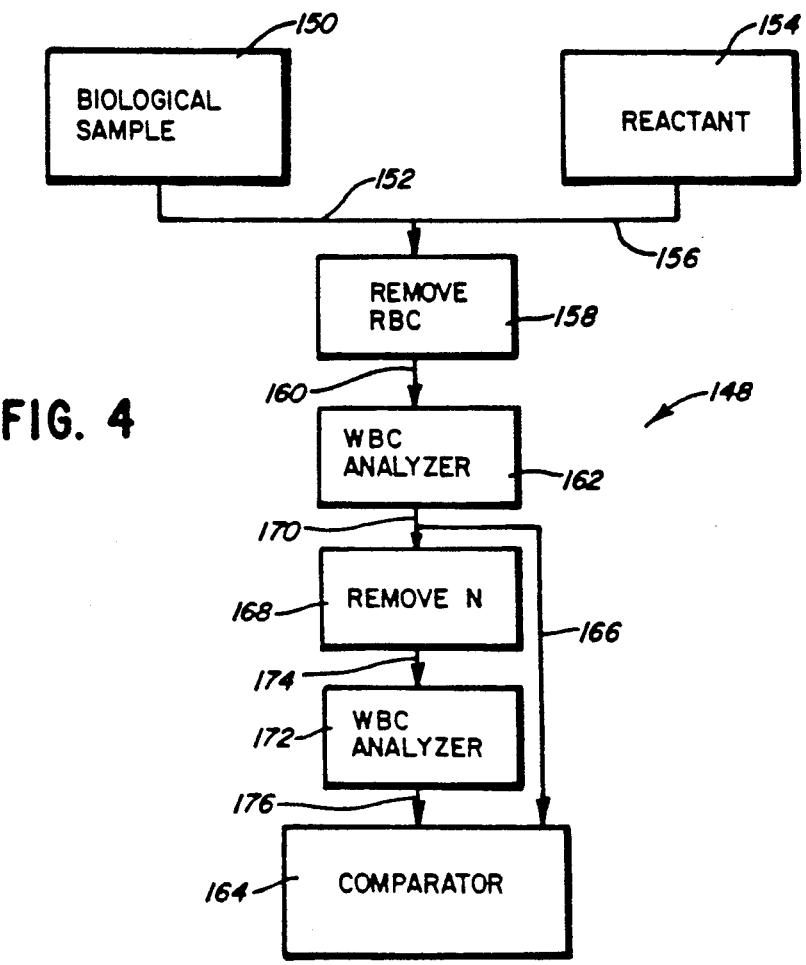
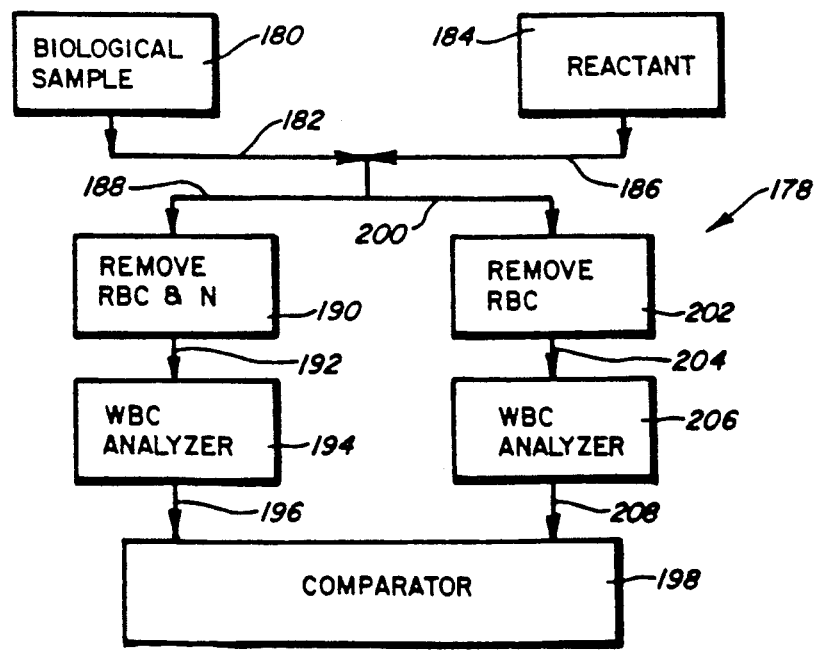

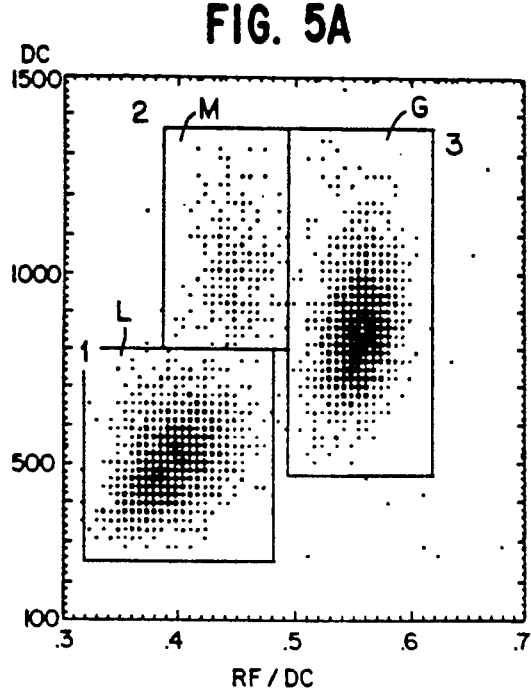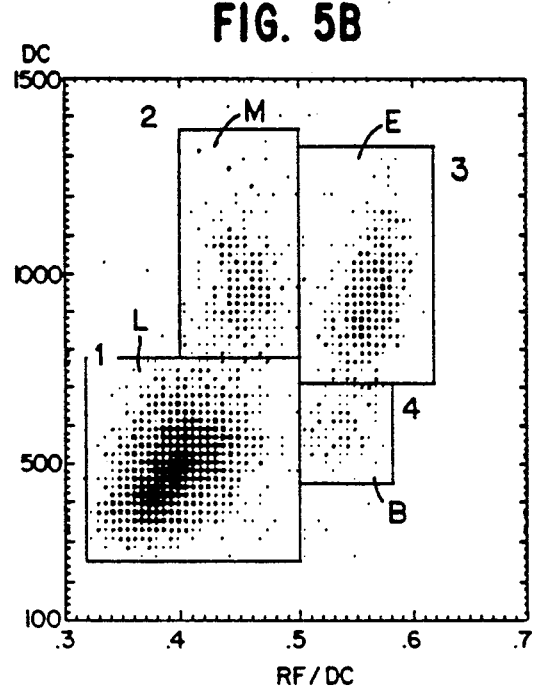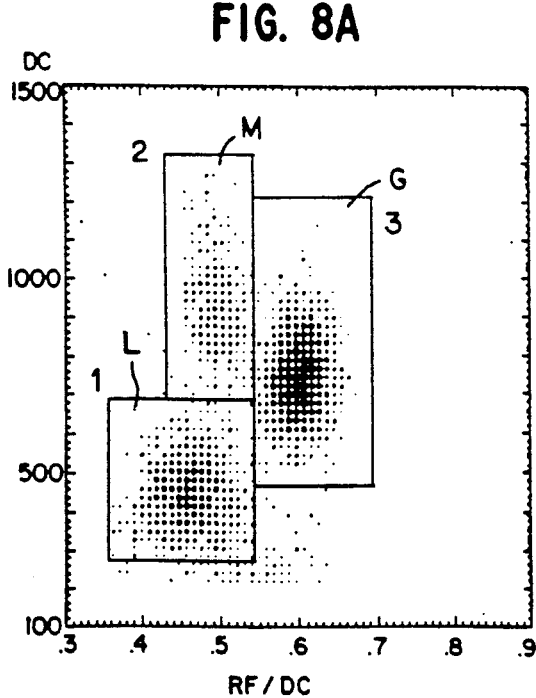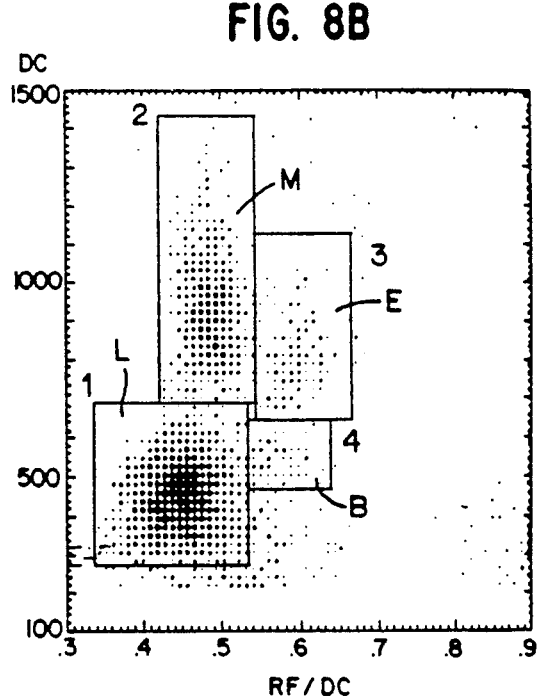

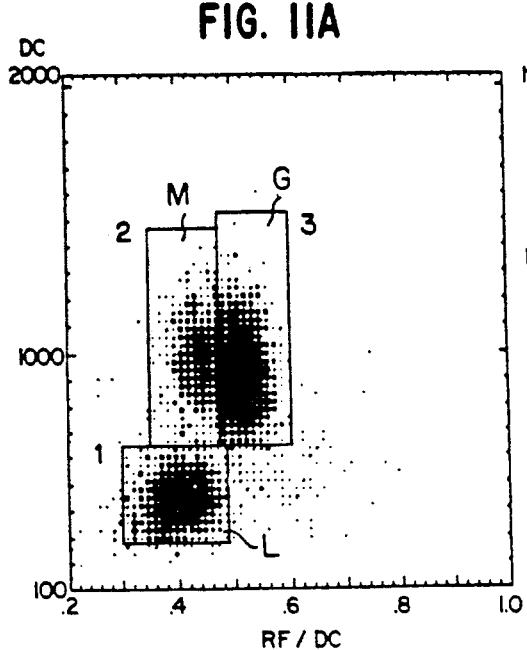
FIG. IIA
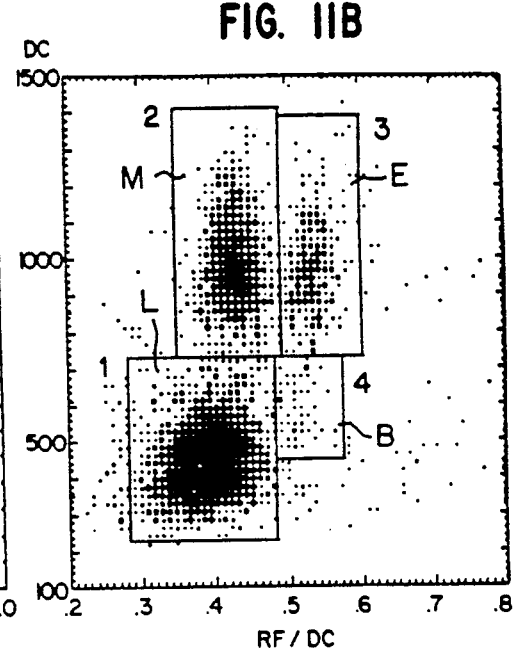
FIG. IIB
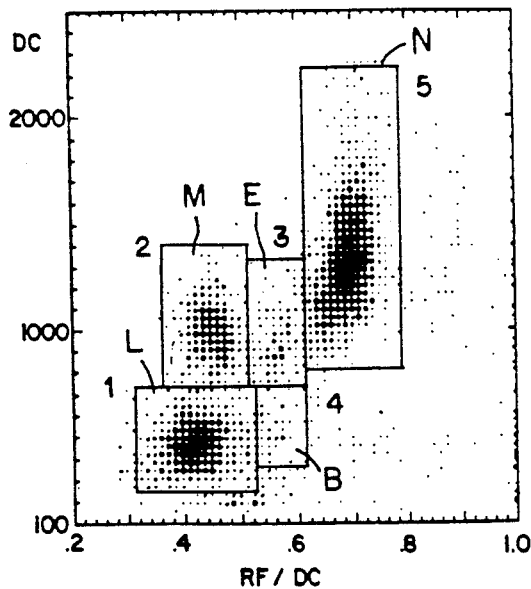
FIG. 13
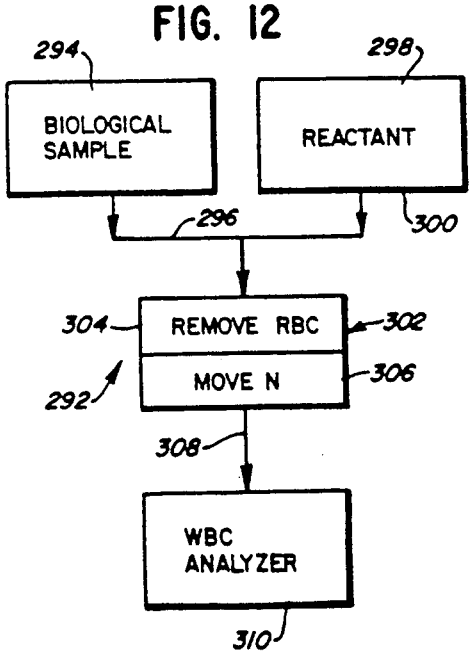
FIG. 12

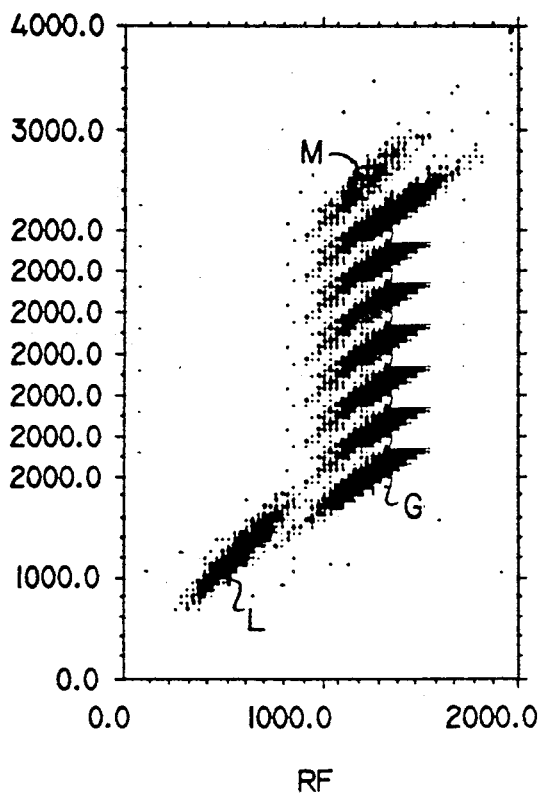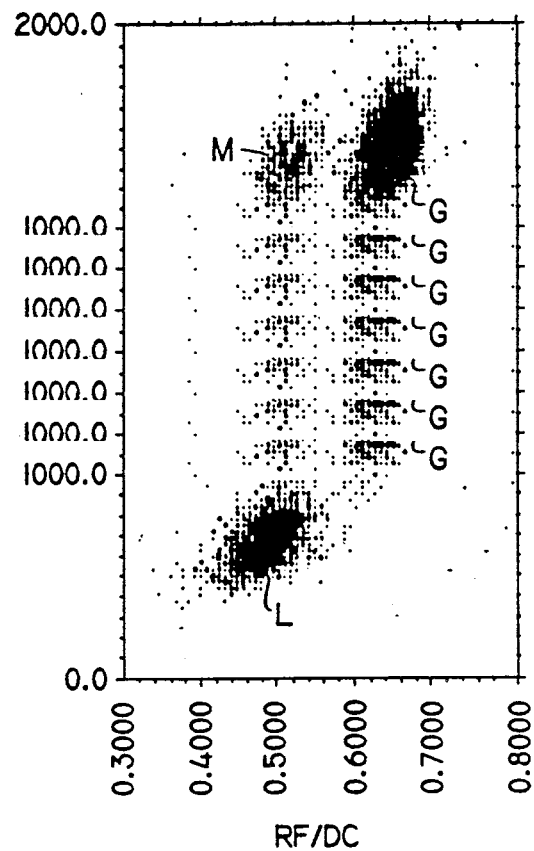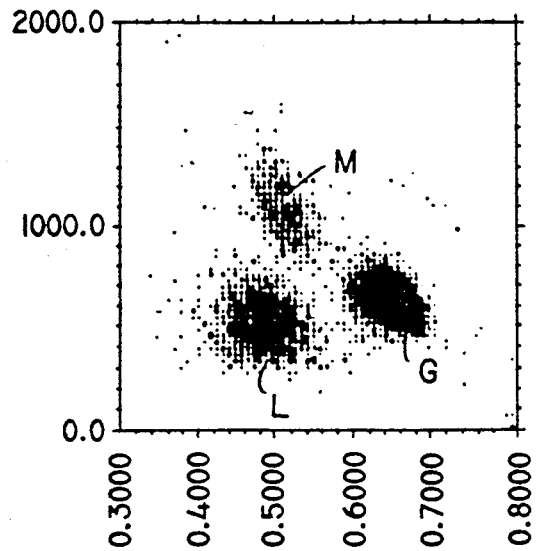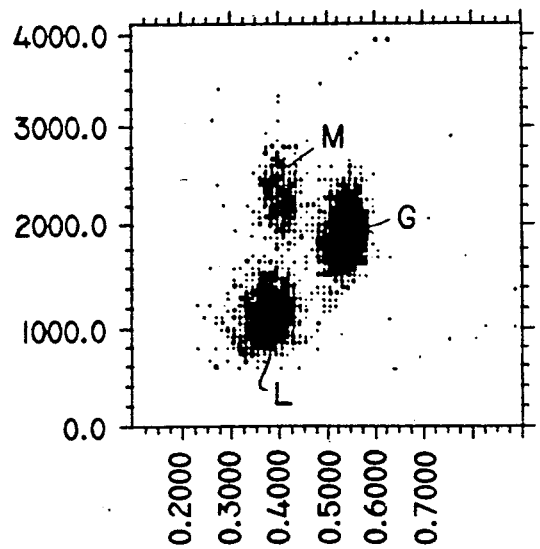

METHOD AND APPARATUS FOR SCREENING CELLS OR FORMED BODIES WITH POPULATIONS EXPRESSING SELECTED CHARACTERISTICS

CROSS-REFERENCE TO RELATED APPLICATION

This ia a continuation of Ser. No. 07/285,856 filed Dec. 16, 1988, now abandoned, which is a continuation-in-part of U.S. Ser. No. 025,345, filed Mar. 13, 1987, which was abandoned in favor of a continuation application U.S. Ser. No. 587,646, filed Sep. 20, 1990 the disclosure of which is incorporated herein by reference.

BACKGROUND OF THE INVENTION

This invention relates generally to a method and apparatus for screening cells or formed bodies for the enumeration of populations which express selected characteristics for research, diagnostic or industrial purposes. More particularly, the invention is directed to a direct analysis of a WBC population and at least one subset thereof, analysis of formed bodies and multipart blood cell analysis, utilizing a combination of electronic technology and microspheres having specific monoclonal antibodies bonded thereto.

This invention relates generally to an automated analyzer and methods of using same for screening biological cells or formed bodies for the enumeration of populations which express selected characteristics for research, diagnostic, medical or industrial purposes. More particularly, the automated analyzers and methods embodying the invention enable multiple part classifications of cells and formed bodies, functional phenotyping of cells and formed bodies, typing of leukemic, lymphoma and solid tumor cells, among others, using a unique combination of electronic technology and the specificity of selective biological molecules, such as antibodies, for such screening and selective enumeration of the cells and formed bodies.

Automation of routine complete blood cell (CBC) analysis of human peripheral blood by an automated blood cell counter was successfully achieved by the COULTER COUNTER ® Model A of Coulter Electronics, Inc. of Hialeah, Fla. The electronic particle sensing system principle of that instrument is disclosed in U.S. Pat. No. 2,656,508 issued Oct. 20. 1953 to Wallace H. Coulter. The use of optical sensing means or lasers, which can be troublesome and expensive, are avoided by particle analyzing instrumentation solely operated on this Coulter electronic sensing principle.

This Coulter sensing principle was developed and expanded into more sophisticated instrumentation such as COULTER COUNTER ® Model S types of instruments which enabled CBC parameters, absolute cell counts, platelet count and morphology, red blood cell (RBC) morphology, interpretation of normal and abnormal blood specimens by special computer programs.

The Coulter electronic particle sensing principle employs an aperture sensing circuit using a direct current (DC) aperture supply. Such particle sensors are simple in structure, extremely rugged and reliable as attested to by the substantially universal acceptance of the COULTER COUNTER ® automated analyzer in clinical laboratories in the United States and throughout the rest of the World. An improvement in this basic aperture sensing circuit was disclosed in U.S. Pat. No. 3,502,974 issued in 1970 to Wallace Coulter and Walter Hogg. In addition to the standard direct current aperture supply, a high frequency aperture current was applied which enabled the sensing of an additional parameter for classification purposes. The high frequency aperture current produced a signal which is the function of the blood cell's internal conductivity as well as its volume. The signal produced simultaneously by the direct current aperture circuit is a conventional DC amplitude signal which provides an indication primarily of cell volume. The radio frequency amplitude is divided by the direct current pulse amplitude employing a high speed divider circuit to obtain a quotient which is a function of cell volume and internal resistance, conveniently referred to as "opacity". This principle is further described in U.S. Pat. No. 3,502,973 also issued to Wallace Coulter and Walter Hogg, in 1970. This parameter has applicability in cell classification systems. Either a single or a pair of separate apertures could be utilized for this purpose.

Classification of different populations is accomplished by collating the data of the signal pairs as they are produced; one, a measure of particle volume and the other a measure of cell internal resistivity or opacity. A convenient form of presenting this data is by two-dimensional plots referred to as scatterplots or scattergrams. Such plots are well described in *Flow Cytometry and Sorting,* page 371; edited by Melamed Melaney, and Medelsohn, 1979, John Wiley & Sons, NY, N.Y.

FIG. 5A is one example of a data plot of a sample of normal blood. Each dot represents an individual cell. The height above the baseline represents the relative volume of the cell. The distance of the dot to the right of the vertical baseline represents the relative opacity. A plot of normal white blood cell (WBC) (with the red blood cells removed) shows three clusters of dots representing three distinct populations which are a consequence of their intrinsic differences in size and internal composition. If desired, with suitable circuitry, these populations can be enumerated to obtain the numbers of each. The cells are classified on the basis of these inherent differences.

Initial applications of the Coulter electronic particle sensing principle was to perform red blood cell counts and then, more sophisticated determinations of other red blood cell parameters. By removing red blood cells from whole peripheral blood, analysis of the white blood cell populations could be undertaken so long as the red blood cell removal did not significantly impair properties of the remaining white blood cell populations sought to be measured. Red blood cell lysing reagents were developed for this purpose which, though useful and widely applied, were not entirely satisfactory in all respects for subsequent white blood cell determinations.

Previous method of flow analysis of leukocytes using DC volume along or light scatter at various angles have shown three clusters of leukocytes corresponding to lymphocytes, monocytes and granulocytes which included the neutrophil, basophil and eosinophil populations. A rough but useful estimation of eosinophil concentration can be made on some samples. The fifth major population is relatively too small for this approach. The eosinophils also have been observed as a distinct cluster using special fluorescence techniques.

These fluorescent techniques were utilized in flow bytometry instruments such as the EPICS ® flow cytometer available from the Coulter Corporation. Such instruments employed the principle of cells moving in a columnar stream bounded by a sheath flow such that cells lined up in single file and passed individually through a laser beam. Light scatter and/or fluorescence signals from the cells were then utilized in classifying cell populations. Staining cells with absorptive or fluorescent dyes made additional cell population classifications possible. The development of instrumentation and fluorochromes for automated multiparameter analysis is further described in R. C. Leif, et al. in Clinical Chemistry, Vo. 23, pp 1492-98 (1977). These developments expanded the number of simultaneous population classifications of leukocytes to four, namely lymphocytes, monocytes, eosinophils and "granulocytes" (neutrophils and basophils).

A more recent analytical hematology instrument has utilized light scattering techniques together with peroxidase enzyme staining (absorptive dye) of cells to produce a five part leukocyte differential. Moreover, dyes in combination with specific reacting biological molecules, such as monoclonal antibodies, have increased the number of leukocyte classifications possible to include functional sub-divisions.

An improved single automated instrument and methods of using the same, is disclosed in parent application, U.S. Ser. No. 025,345, filed Mar. 13, 1987, which was abandoned in favor of a continuation application U.S. Ser. No. 587,646, filed Sep. 20, 1990 entitled AUTOMATED ANALYZER AND METHOD FOR SCREENING CELLS OR FORMED BODIES FOR ENUMERATION OF POPULATIONS EXPRESSING SELECTED CHARACTERISTICS. The parent application combines the application of electronic sensing aperture principles, the specificity of selective biological molecules for identifying and/or enumerating defined populations of cells or formed bodies and microscopic particle technology. The automated analyzer can be used together with a special lysing reagent and/or antibodies coupled to microscopic microspheres or supports of varying composition.

Selectively attaching microscopic particles makes possible the modification of the parameter(s) responsible for the original location of at least one of the populations. The bulk addition of microscopic particles to selected target populations where this addition affects the measured volume and/or opacity results in shifting the location of the dots representing a population.

Antibodies of known specificity are employed in coating microscopic particles. This coating gives the particle the capacity to selectively attach to certain cells which express the antigen the antibody is specific for. These coated or tagged cells are a combination of particles and cell which behave like a new entity. Their parameters of opacity, volume, or both opacity and volume may be considered to represent the sum of the effects of both the cell and the particles on the signals obtained. If the characteristics of the components are different, the new entity will move to a new position in accordance with the net effect. The new location, in contrast with the former position of the cell alone, should allow a classification of such new entity or group of new entities. If the particles attached to the cells are magnetic, then of course, according to current practice, the new entities can be captured by the use of a magnet. If mixed rapidly, unexpected results including complete capture of a population without adversely affecting the properties of the cells under study occur.

Only three distinct populations of cells can be readily identified and enumerated from a blood sample by utilizing their inherent and unique properties of DC volume and opacity parameters heretofore stated. Additional steps, such as improved lysing systems, must be taken to enable the detection and enumeration of more populations. Of course, these additional populations represent subpopulations of the three basic ones referred to as lymphocytes, monocytes and granulocytes. The steps performed in accordance with the parent application demonstrate how subpopulations of these basic three populations are obtained.

Employing such simple aperture sensing techniques in combination with two or more biological particles, one can produce a unique and new position of the dot cluster representing a given population. This selective movement of populations on the dot plot or scattergram is reproducible and can be used to classify a population separate from the basic three populations.

The original and inherent combination of DC volume and opacity sensing techniques can be modified through the attachment of microscopic particles to selected individual cells. The selectivity is given the particles by the nature of specificity of the biological molecules, antibodies among others, employed as the coating on their surfaces. A population of cells along, having no particles on their surface, may occupy a dot plot position no different from other populations or subpopulations and, henceforth, not be distinguishable from one another. The addition of particles having a selective attraction to a specific population of cells which one seeks to identify, enumerate, and study is possible using this approach. The selective addition of a sufficient mass of selective particles to a distinct population of interest results in the shifting of that population's dot plot location as a result of the new and unique combination of mass, volume and opacity.

The separation of specific cell populations is accomplished without materially affecting the properties of remaining cell populations. For example, the removal of erythrocytes or red blood cells (RBC's) from whole blood in accordance with this invention permits the measurement of T4 and/or T8 lymphocytes not otherwise possible with heretofore available chemical RBC lysing reagents. Ratios of the number of T4 versus T8 cells have been used to indicate immune deficiencies consistent with severe viral infections including the AIDS virus among others. The presence of specific receptors on the surface of cells can be used to classify a population into subsets, whose enumeration permits the detection of the onset of disease. For example, in the predominant forms of leukemia there is a sharp rise in peripheral blood lymphocytes. If the subpopulation of lymphocytes which is rapidly proliferating bears the T11 receptor, the patient is at risk of immune abnormalities. Further, if the subpopulation of T11 positive lymphocytes is T4 receptor bearing, then the patient is classified as that common in Japan. Moreover, if the T4 receptor subpopulations expanding is 2H4 positive, then the patient will not only demonstrate a tendency of multiple infections but acute leukemia as well for the T11, T4, 2H4 positive cell is the inducer of suppression and functionally inhibits the patient's ability to make antibodies. Therein, the patient is subject to multiple infections and must be treated for both leukemia and immune deficiency. K. Takatsuki, et al., GANN monograph on Cancer Research 28:18-22, 1982; C. Morimoto, et al., Coulter Japan Symposium, 1984; C. Morimoto, et al., Immunology 134 (3):1508-1515, 1985; C. Morimoto, et al., New England Journal of Medicine 316(2):74-71, 1987. The invention also applied to analyses of formed body suspensions such as bacteria and viruses among others.

The method and apparatus embodying the invention can be utilized with a variety of immunological reactions, such as immunological reactions involving reactants and formed bodies or cells. As utilized herein, cells are defined as animal or plant cells, which are identifiable separately or in aggregates. Cells are the least structural aggregate of living matter capable of functioning as an independent unit. For example, human RBC and WBC populations, cancer or other abnormal cells from tissue or from blood samples. Formed bodies are defined as bacteria, viruses and fungi which also can include a substrate. The invention can be utilized in diagnosing, monitoring or treating of patients. The invention specifically can be utilized to eliminate or shift populations to analyze populations or subpopulations which cannot otherwise easily be identified. The cells and formed bodies suitably tagged or labeled reasonably can be expected to be sensed by the method and apparatus of the invention in the same manner as the human blood cell examples. The change in parameter can be sensed without regard to the substrate or lack thereof.

This invention provides a single versatile analyzer and methods of using same which combines electronic particle sensing technology and the specificity of selective biological molecules to enable a major advancement in the field of automated analyzers for clinical laboratory use, and for industrial applications. The detection of multiple leukocyte subpopulations, and their relationship to one another in human peripheral blood is important in medical research and the diagnosis of human diseases. Such data are useful as a screening tool for identifying and classifying diseases, such as leukemia. Abnormal situations identified by implementation of the invention herein provides diagonally relevant information in areas of study not limited only to detection of leukocyte populations as will be apparent from the specification and drawings hereof.

One of the most valuable features of this invention is that it employs the single rugged Coulter sensing operation. It is stable and does not require the complexity and expense of optical systems. The circuitry required for the addition of the RF generator and detector is economical, compact and reliable. A single aperture is all that is required, but the addition of a second or even a third aperture can enable a greater sample throughput rate economically.

SUMMARY OF THE INVENTION

The invention provides a method and apparatus for performing screening of cells or formed bodies for enumerating populations to identify selected characteristics or properties expressed by the cells or formed bodies or subsets thereof. A multipart or five part white blood cell differential can be performed from a whole blood sample or from a sample with the red blood cells and/or populations of the white blood cells removed. A whole blood sample or portion thereof can be screened to provide a direct analysis of a WBC population and at least one WBC population subset thereof. The RBC population is removed or preremoved from the sample without substantially affecting the characteristic of interest of the WBC population and subset thereof.

The volume and/or opacity parameters of at least the WBC population subset of interest are modified and then at least the population and subset thereof are electronically analyzed to determine at least one characteristic of the WBC population. At least one WBC population subset can first be subtracted from the sample prior to analyzing of the population and subset thereof. Two subsets can be modified at the same time by providing different sized microspheres to bind to each subset. Further, a plurality of microspheres can be bound to each of the cells of the WBC subset of interest. These procedures provide direct WBC analyses including any desired subset thereof without the use of optical/light techniques.

BRIEF DESCRIPTION OF THE DRAWINGS

FIGS. 1-13 describe the embodiments disclosed in parent application Ser. No. 025,345;

FIG. 1 is a schematic block diagram of one cell population analyzer embodiment of the parent application;

FIG. 2 is a schematic block diagram of a second analyzer embodiment of the parent application;

FIG. 3 is one specific analyzer embodiment of the parent application corresponding to FIGS. 1 and 2;

FIG. 4 is a schematic block diagram of another analyzer embodiment of the parent application;

FIG. 5A and 5B are a scattergram of one set of results utilizing a prototype analyzer system similar to that illustrated with respect to FIGS. 2 and 3;

FIG. 6 is a schematic block diagram of a further analyzer embodiment of the parent application;

FIG. 7 is a schematic block diagram of a still further analyzer embodiment of the parent application;

FIGS. 8A and 8B, 9A and 9B, 10A and 10B and 11A and 11B are a scattergram of one set of results utilizing a prototype analyzer system similar to that illustrated with respect to FIGS. 6 and 7;

FIG. 12 is a schematic block diagram of a yet still further analyzer embodiment of the parent application;

FIG. 13 is a scattergram of one set of results utilizing a prototype analyzer system similar to that illustrated with respect to FIG. 12;

FIGS. 14-26D are directed to embodiments of the present invention;

FIG. 14 is a schematic block diagram of one WBC population subset analyzer embodiment of the invention; FIG. 15 is another schematic block diagram of a WBC population subset analyzer embodiment of the invention;

FIG. 16 is one specific analyzer embodiment of the invention corresponding to FIGS. 14 and 15;

FIGS. 19 A-D, 20A—D and 21A-D are scattergrams of the CD4, CD8, CD2 and CD20 subset populations of samples of different patients;

FIGS. 26A-D are scattergrams of the same populations illustrated on different parameter scattergrams.

DESCRIPTION OF THE PREFERRED EMBODIMENTS

FIGS. 1-13 describe the embodiments of the parent application, Ser. No. 025,345, now U.S. Ser. No. 587,646.

Figure 1:
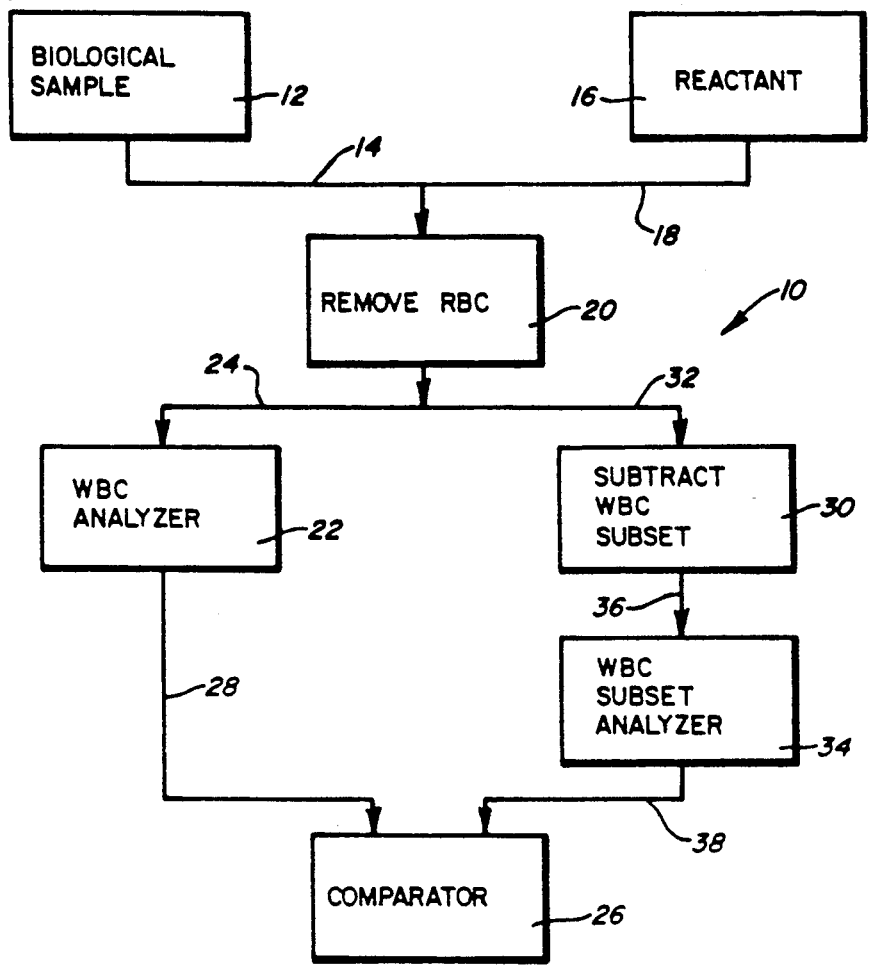

Referring to FIG. 1, a first embodiment of a cell population analyzing method and apparatus of the parent application, Ser. No. 025,345, is designated generally by the reference numeral 10. The analyzer 10 includes a biological sample 12 which contains at least a first set of viable biological cells (not illustrated), such as in or from a whole blood sample. The cells of the biological sample 12 are to be involved in a biological reaction in a quantitative and/or qualitative determination or analysis. The sample 12 can include a buffer into which the cells are added.

The sample 12 is combined via a line 14 with at least one reactant 16 via a line 18. The red blood cells (RBC) then are removed form the mixture by a functionally designated RBC removing station 20. The RBC's can be removed from the mixture by the station 20 in a number of ways. The RBC's can be lysed by a lyse in the reactant 16. One such preferential lyse and a quench which can be utilized therewith is disclosed in Ser. No. 109,643, filed Nov. 13, 1990, which is a continuation of Ser. No. 130,911, filed Dec. 10, 1987, entitled METHOD AND REAGENT SYSTEM FOR ISOLATION, IDENTIFICATION AND/OR ANALYSIS OF LEUKOCYTES FROM WHOLE BLOOD SAMPLES, which is a CIP of Ser. No. 025,303, filed Mar. 13, 1987, of the same title, which are incorporated herein by reference. The reactant 16 can be or include a plurality of magnetic microspheres with an antibody specific to the RBC's bound to the microspheres (not illustrated). In this example, the particular red blood cell specific antibody utilized is disclosed in application Ser. No. 799,489, filed Nov. 19, 1985, now U.S. Pat. No. 4,752,563, entitled MONOCLONAL ANTIBODY FOR RECOVERY OF LEUKOCYTES IN HUMAN PERIPHERAL, BLOOD AND METHOD OF RECOVERY EMPLOYING SAID MONOCLONAL ANTIBODY, which is incorporated herein by reference. The reactant 16 also can include a buffer in addition to or in place of the sample buffer. The reactant 16 further can be a combination of the preferential RBC lyse and the RBC specific microspheres.

Once the RBC's substantially are removed from the mixture, a portion of the mixture is fed into a white blood cell (WBC) analyzer 22 via a line 24. The WBC analyzer 22 at least counts the number of WBC's in the mixture. The WBC analyzer 22 also can measure one or more volume or opacity parameters of the WBC's. The results from the analyzer 22 are fed to a comparator 26 via a line 28.

A second portion of the RBC deleted mixture is fed to a WBC subset subtracting station 30 via lien 2. The WBC's can be subtracted from the mixture in a number of ways. Microspheres with a monoclonal antibody specific to one of the WBC subsets bound thereto can be added to the mixture. Non-magnetic microspheres can be bound to the WBC's to change or shift the resultant opacity or volume parameters of the cells. Magnetic microspheres also can be bound to the WBC's which then can be removed from the mixture by a magnetic field.

The mixture with the WBC subset population removed for with one or more parameters changed then is fed to a WBC subset analyzer 34 via a line 36. The analyzer 34 can be identical to the analyzer 22. The results of the analyzer 34 then are fed to the comparator 26 via a line 38. The comparator 26 then can compare the WBC results from the analyzer 22 with the modified results from the analyzer 34 to determine at least one characteristic of the selected white blood cell population, such as the number of cells in a particular range.

Figure 2:
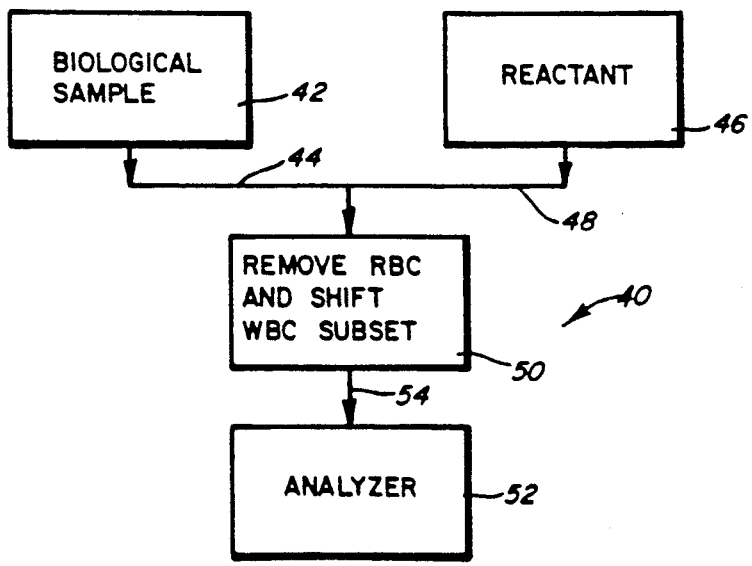

Referring to FIG. 2, a second embodiment of a cell population analyzing method and apparatus embodying the parent application is designated generally by the reference numeral 40. The analyzer 40 includes a biological sample 42 which again contains at least a first set of viable biological cells (not illustrated), such as in or from a whole blood sample. The cells of the biological sample 42 are to be involved in a biological reaction in a quantitative and/or qualitative determination or analysis. The sample 42 again can include a buffer into which the cells are added.

The sample 42 is combined via a line 44 with at least one reactant 46 via a line 48. In the analyzer 40, the RBC's are removed from the mixture and simultaneously at least one characteristic of at least one WBC subset is changed or shifted by a functionally designated RBC removing and WBC shifting station 50. As stated above, the RBC's can be removed from the mixture by the station in a number of ways, previously enumerated with respect to the station 20. Simultaneously, in the same mixture portion, the WBC's are bound to, generally non-magnetic, microsphere to change or shift the resultant opacity and/or volume parameters of the cells.

The mixture with the RBC's removed and the WBC subset population shifted then is fed to an analyzer 52 via a line 54. The analyzer 52 can be substantially identical to the analyzer 22. The analyzer 40 thus provides a fast, direct analysis of at least one characteristic of a selected WBC population or whole blood subset.

One specific embodiment of an analyzer instrument embodying the parent application and which can accomplish the analyzing methods of the first and second analyzer 10 and 40, is designated generally by the reference numeral 56 in FIG. 3.

In the instrument 56, only one specific enumeration is illustrated, which can be varied in almost endless detail in accordance with the principles of the parent application. Further, the instrument 56 is shown in generally functional detail and the specific embodiments can be structurally implemented in many known ways.

The instrument 56 includes an aspirator pumping mechanism 58 which is utilized to draw the biological sample of interest, for example the sample 12 or 42 into the instrument 56. The aspirator 58 is coupled via a line 60 to a sampling valve 62, which can be coupled to a sample probe 63. A lyse pump 64 can include the lyse, such as part of the reactant 18 or 46 and is also coupled to the valve 62 via a line 66. The valve 62 and the pump 58 can aspirate the biological sample 12 or 42 along with the lyse via the pump 64 when appropriate.

The reactant mixture or the biological sample itself, then is fed via a discharge line 68 into a mixing apparatus 70. The mixer 70 includes a mixing chamber 72 into which the sample or reactant is fed. At this point the operation of the analyzer 10 and 40 differ and hence will be described separately.

In the case of the analyzer 10, if the RBC's have been lysed by the lyse from the pump 74, then when the reaction is completed a quench or fix is supplied from a station 74 via a line 76. The reaction can be assisted by mixing the lyse and the sample in the chamber 72 as illustrated functionally at 78.

Specific details of an appropriate mixing apparatus 70, which can be utilized herein are disclosed in Ser. No. 517,309, filed May 1, 1990, which is a continuation of Ser. No. 025,337, filed Mar. 13, 1987, entitled METHOD AND APPARATUS FOR RAPID MIXING OF SMALL VOLUMES FOR ENHANCING BIOLOGICAL REACTIONS, which is incorporated herein by reference. By utilizing the mixer 70 the reactions are greatly enhanced in speed without significantly damaging the properties of interest of the cells, such as, can occur by raising the reaction temperature. Further, the reactions generally are completed in significantly less than a minute, generally on the order of fifteen seconds or less. This allows a rapid analysis of the automatic high volume analyzer instrument 56.

The quenched reactant with the RBC's removed by the lyse (as from the station 20) then is fed via a line 80 to a holding chamber 82, which in this case will hold a second portion of the mixture. A first portion of the mixture will be fed from the chamber 82 via a line 84 to a WBC analyzer 86 (i.e. analyzer 22). The analyzer 86 can be of many physical types in accordance with the counting and sizing techniques described by Wallace H. Coulter in U.S. Pat. No. 2,656,508 and embodied in the numerous commercial blood cell counter of the assignee, Coulter Electronics, Inc.

The analyzer 86, in general, includes a flow sensor or sensing chamber 88. The chamber 88 includes a transducer 90 which has an aperture 92 therethrough. The chamber 88 includes a first portion 99 which has a first electrode 96 in contact with the fluid therein.

The chamber portion 94 and the electrode 96 communicate through the aperture 92 with a second chamber portion 98 having a second electrode 100 therein.

The electrodes 96 and 100 are coupled via reactive leads 102 and 104 to an RF/DC source and sensing circuit 106. The circuit 106 coupled both a DC, or low frequency current or signal, and a high frequency signal between the electrodes 96 and 100.

The low frequency signal is utilized to sense the amplitude of a signal pulse caused by a cell passing through the aperture 92. The high frequency signal is utilized to obtain the electrical opacity of the same cell passing through the aperture 92.

The measuring of the electrical opacity of cells was described by Wallace H. Coulter and Walter R. Hogg in U.S. Pat. No. 3,502,974 and several patents and publications of the assignee, Coulter Electronics, Inc., since that patent. One specific circuit which can be utilized herein is disclosed in U.S. Pat. No. 4,791,355, entitled PARTICLE ANALYZER FOR MEASURING THE RESISTANCE AND REACTANCE OF A PARTICLE, filed Oct. 21, 1986, U.S. Ser. No. 921,654, which is incorporated herein by reference.

The signals generated by the circuit 106 from the sensed cells are coupled via a DC signal lead 108 and an RF signal lead 110 to a comparator 112 (like the comparator 26). The comparator 112 can hold the signal generated from the first portion, i.e. those without the WBC subset substracted, for a comparison with the results from the second portion to be described.

The analyzer 86 can include a sheath flow to focus the cells in the sensor 88, in the well known manner. The sheath flow can be provided by a fluidic system 114, coupled to the sensor 88 by a pair of lines 116 and 118 in a known manner. The sample reaction mixture can be fed into the sensor 88 via an introduction tube 120 and can be fed from the sensor 88 via an exit tube 122 into a waste container 124.

While the first portion of the mixture was being analyzed in the analyzer 86, the second portion is held in the chamber 82, while the mixer 72 is cleaned or flushed via a rinse line 126 and exhausted through a waste line 128. Once the chamber 72 is cleaned, the second portion is fed back into the chamber 72 via a line 130. Like the station 30, the WBC subset now is subtracted by adding the WBC microspheres from a station 132 via a line 134, a valve 136 and a chamber line 138.

The WBC microspheres are mixed with the second portion by the mixing mechanism 78. If the WBC microspheres are non-magnetic, the reaction mixture with the bound WBC microspheres is fed via the line 80, the chamber 82 and the line 84 into the analyzer 86, (i.e. the analyzer 34), wherein the second portion is analyzed like the first portion and the results then are compared it he comparator 112 (i.e. the comparator 26). At least one of the WBC subset cell parameters is changed in the second portion, such as the cell opacity by the WBC subset bound microspheres to provide the changed results which then can be analyzed.

If the WBC microspheres are magnetic, then the WBC subset bound thereto are removed by a magnetic field during and/or after the mixing process by a magnetic field or magnet 140. The field can be provided by electromagnetic means or by the magnet 140 being physically moved with respect to the chamber 72 to capture the magnetically bound WBC subset. The second portion without the bound WBC subset then is fed via the line 80, the chamber 82 and line 84 to the analyzer 86 in the manner previously described to obtain the analysis (like the analyzer 34).

The instrument 56 then is prepared to take the next sample for the next analysis. The probe 63 can be cleaned by a probe rinse mechanism 142 and the lines and chambers 72 and 82 can be flushed in a conventional manner. Each analysis of the succeeding sample mixture is obtained in a rapid and automatic fashion. The period between the analysis of succeeding sample mixtures can be on the order of minutes or less.

In operating the analyzer instrument 56, like the analyzer 40, the reaction mixture with the RBC lyse/reactant 46 and the sample 42 is mixed in the chamber 72 along with non-magnetic WBC microspheres from the station 132, which bind to one of the WBC subsets. The quench 74 is added to the reactive mixture which then is fed via the lien 80, the chamber 82 and the line 84 to the WBC analyzer 86 for analysis (i.e. like the analyzer 52).

Alternatively to the utilization of the lyse, in either of the analyzers 10 and 40, the sample 12 or 42 can be fed to the mixer 70 via the valve 62 without any lyse. In this case the RBC's can be removed magnetically by utilizing the microspheres with the RBC specific antibody bound thereto from an RBC microsphere station 144 and fed to the valve 136 via a line 146 and hence to the chamber 70 via the line 138. Where no lyse is utilized, the bound RBC's are magnetically removed by the magnet 140 after mixing in a manner substantially identical to the magnetically bound WBC's described above.

Further, in a second case to promote the speed of the reaction, a reaction mixture of the sample with both the RBC lyse and with the RBC magnetic beads can be utilized. The reaction mixture is mixed, the lyse is quenched and the bound RBC's are magnetically removed and then the WBC's are analyzed as previously described.

Referring now to FIG. 4, another embodiment of a cell population analyzing method and apparatus embodying the parent application is designated generally by the reference numeral 148. The analyzer 148 includes a biological sample 150 which again contains at least a first set of viable biological cells, such as in or from a whole blood sample. The sample 150 again can include a buffer into which the cells are added.

The sample 150 is combined via a line 152 with at least one reactant 154 via a lien 156. The RBC's then are removed as above described by a functionally designated RBC removing station 158. The reaction mixture with the RBC's removed is fed via a lien 160 into a WBC analyzer 162. The results from the analyzer 162 are fed to a comparator 164 via a line 166, providing a three-part WBC differential with results for monocytes (M), lymphocytes (L) and granulocytes (G).

The mixture then is fed to a neutrophil (N) functionally designated removal station 168 via a line 170. The N's can be removed from the mixture by shifting or changing one parameter, such as opacity, or by magnetic removal, both as described above. In this example, the particular N specific antibody utilized is disclosed in MONOCLONAL ANTIBODY SPECIFIC TO NEUTROPHILS, filed Dec. 8, 1986, U.S. Ser. No. 938,864, abandoned in favor of continuation-in-part application U.S. Ser. No. 070,202, now U.S. Pat. No. 4,931,395.

The mixture with the N's removed or shifted then is fed to another WBC analyzer 172 via a lien 174. The results of the analyzer 172 are fed to the comparator 164 via a line 176. The results of the analyzer 172 are utilized to obtain a four-part WBC differential with results again for M's and L's, but now in addition since the N's are shifted or removed results for eosinophils (E) and basophils (B) are obtained. The two analytical results from the analyzers 162 and 172 then can be compared by the comparator 164 to form a five-part WBC differential. Specifically, subtracting the number of B's and E's from the number of Gr's results in the number of the removed N's.

Referring now to FIGS. 5A and 5B, two sets of scattergram results are illustrated obtained from a whole blood sample utilizing a prototype analyzing method similar to the analyzer 148. The biological sample 150 was a 20 microliter sample of whole blood, which was combined with 40 microliters of the magnetic microspheres with the RBC specific antibody bound thereto combined with 140 microliters of buffer solution to form the reactant 154. The reaction mixture was mixed for 15 seconds and placed in a magnetic field for 10 seconds in the station 158. The mixture with the RBC's removed was analyzed by the analyzer 162 as illustrated in the scattergram of FIG. 5A resulting in counts of L's of 45.6 (1), M's of 5.6 (2) and Gr's of 48.7 (3).

The mixture then is combined it the station 168 with 10 microliters of magnetic microspheres with the N specific antibody bound thereto. The mixture is mixed 30 seconds and then placed in a magnetic field for 10 seconds. The mixture with the N's then removed was fed to the analyzer 176 which resulted in the scattergram of FIG. 5B resulting in counts of L's of 81.0 (1), M's of 0.6 (2), E's of 11.0 (3) and B's of 1.8 (4). The comparator 164 then provides the five-part WBC differential of counts of 45.6 L's, 5.6 M's, 41.6 N's, 6.0 E's and 1.2 B's. This corresponds to a standard microscopic five-part WBC differential utilizing Wright stain on the sample on a slide resulting in counts of 44.0 L's, 3.4 M's, 45.0 N's, 6.1 E's and 0.4 B's.

FIG. 6 illustrates a further embodiment of a cell population analyzing method and apparatus embodying the parent application, designated generally by the reference numeral 178. The analyzer 178 includes a biological sample 180 which again contains at least a first set of viable biological cells and also can include a buffer.

The sample 180 is combined via a line 182 with a reactant 184 via a line 186. Functionally illustrated, a first portion of the mixture is fed via a line 188 to a functionally designated RBC and N removing station 190. The RBC's and N's are removed or shifted as described before and the first portion is fed via a lien 192 to a WBC analyzer 194.

This provides a result from the analyzer 194 which is fed via a line 196 to a comparator 198. The result includes the above-referenced four-part differential including M's, L's, E's and B's.

At the same time, a second portion of the mixture of the sample 180 and the reactant 184 is fed via a line 200 to a functionally designated RBC removal station 202. The mixture with the RBC's removed is fed via a line 204 to another WBC analyzer 206. The results of the analyzer 206 are fed to the comparator 198 via a lien 208. The results of the analyzer 206 directly include the above-referenced three-part WBC differential including M's, L's and Gr's. The results of the analyzers 194 and 206 then are compared by the comparator 198 to provide the five-part WBC differential.

Figure 7:
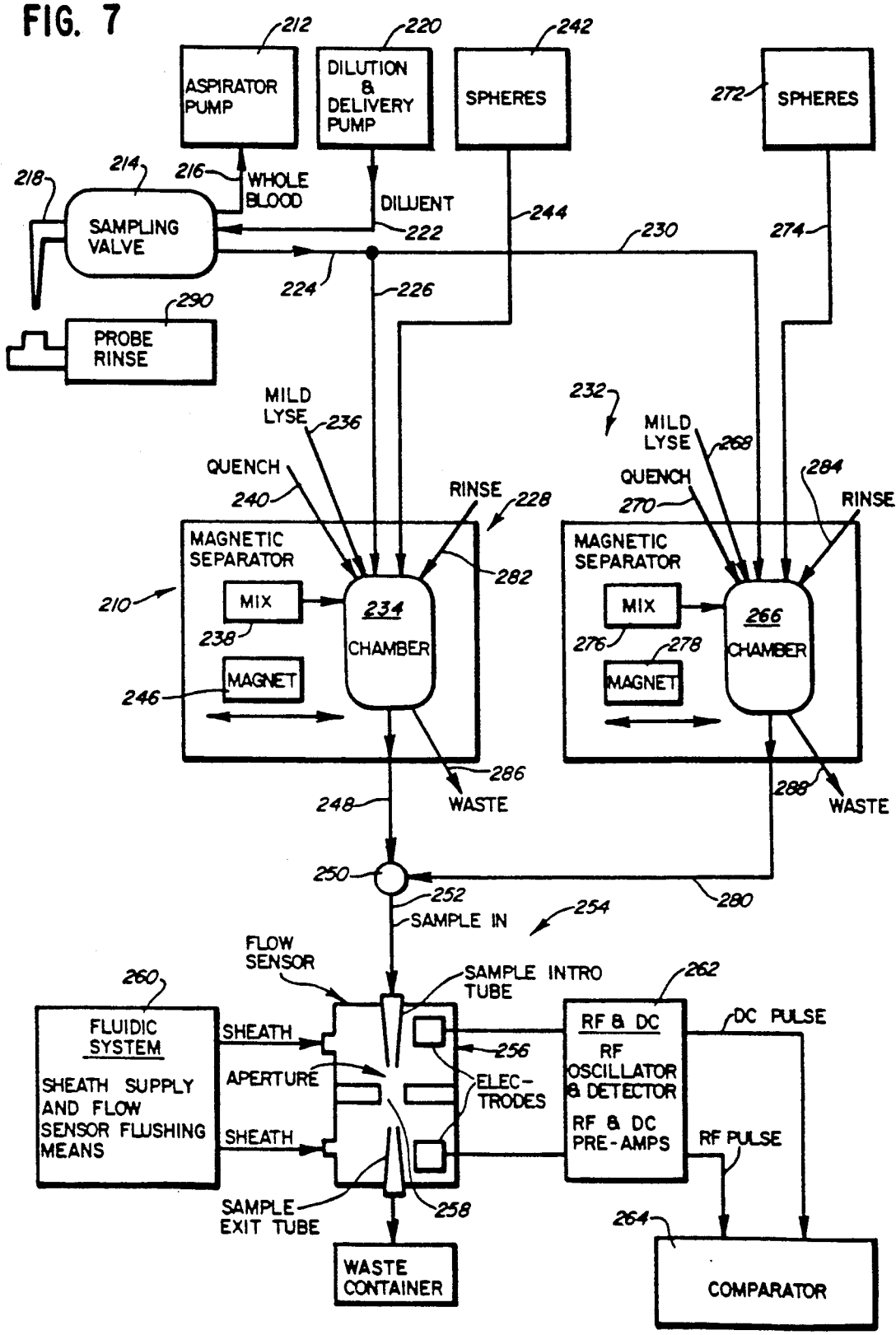

A specific analyzing instrument embodiment incorporating the method and apparatus of the analyzer 178 is designated generally by the reference numeral 210 in FIG. 7. Again, only one specific hardware enumeration has been illustrated, but like the analyzing instrument 56, the analyzing instrument 210 can be implemented in numerous configurations.

The instrument 210 includes an aspirator purging mechanism 212 which is coupled to a sampling valve 214 via a line 216. The valve 214 can include a sample probe 218 to aspirate the biological sample of interest, such as the sample 180. A diluent delivery pump 220 is coupled to the valve 214 via a line 222 to provide a diluent for the sample, such as a whole blood sample, when desired. A first portion of the mixture then is coupled via a line 224 and a line 226 to a first mixing apparatus 228. At the same time, a second portion of the mixture is fed via the line 224 and a line 230 to a second mixing apparatus 232.

The mixer 228 (comparable to the station 190) is substantially identical to the mixer 232 (comparable to the station 202) and will be described first. The mixer 228 includes a mixing chamber 234 into which the first mixture portion is fed. The mixer 228 includes all of the various options above described and can include a lyse input line 236 for the RBC lyse if desired.

If the lyse is utilized, after mixing as illustrated functionally at 238, then the quench is added via a quench line 240. At the same time, the N's are being removed by the addition of the appropriate magnetic or non-magnetic microspheres with the N specific antibody bound thereto from a source of microspheres 242 fed to the chamber 234 via a line 244. If the magnetic microspheres are utilized for the N's or the RBC's, then a magnet 246 or magnetic field is utilized to remove the magnetically bound cells.

The mixed and quenched (where necessary) mixture then is fed via a line 248 through a valve 250 and lien 252 to a WBC analyzer 254 (i.e. analyzer 194). The analyzer 254 is the same as the analyzer 86 and will not be described again in such detail. Again, the analyze 254 includes a sensing chamber 256 with an aperture 258 therein through which the mixture and cells pass. A sheath flow fluidic system 260 can be coupled to the chamber 256. The signals generated by the cells are detected by an RF/DC source and sensing circuit 262 whose outputs are fed to a comparator 264, as previously described.

Concurrently, the second mixture portion is fed into a mixing chamber 266. In the second portion, only the RBC's are removed (i.e. like the station 202) and the RBC's can be removed by the RBC lyse fed into the chamber 266 via a line 268. The lyse is mixed with the sample and then a quench is added via a quench line 270. Alternatively the RBC's can be removed by magnetic microspheres having the RBC specific antibody bound thereto from a microsphere source 272 fed into the chamber 266 via a line 274. The microspheres are fixed, functionally at 276, and then the magnetically bound RBC microspheres are removed by a magnet 278.

The RBC removed mixture then is fed via a line 280 to the valve 250 and via the lien 252 to the analyzer 254 to obtain the above-mentioned results. The mixers 228 and 232 include appropriate respective rinse lines 282 and 284 and waste lines 286 and 288 and a probe rinse 290 to cleanse the instrument 210 prior to aspirating the next sample or sample for analyzing.

FIGS. 8A and 8B illustrate scattergram results obtained from a whole blood sample utilizing an analyzing method similar to the analyzer 178. In this example, 20 microliters of whole blood form the sample 180, while 40 microliters of magnetic microspheres with the RBC specific antibody bound thereto combined with 140 microliters of buffer solution form the reactant 184. A portion of the mixture is mixed for 20 seconds in the station 202 and then placed in a magnetic field for 10 seconds. The RBC removed mixture then ia analyzed in the analyzer 206 resulting in the scattergram of FIG. 8A which provides a count of L's 29.4 (1), M's 8.1 (2) and Gr's 62.4 (3).

At the same time, another portion of the same mixture is combined with 10 microliters of magnetic microspheres with the N specific antibody bound thereto to remove the RBC's and N's in the station 190. The mixture is mixed for 30 seconds, then placed in a magnetic field for 10 seconds. The mixture with the N's and RBC's removed then is analyzed by the analyzer 194 resulting in the scattergram of FIG. 8B which provides a count of L's 73.6 (1), M's 21.7 (2), E's 3.4 (3) and B's 1.4 (4). The two counts are compared in the comparator 198, resulting in a five-part WBC differential count of L's 29.4, M's 8.0, N's 60.8, E's 1.2 and B's 0.6. A microscope comparison again was made resulting in counts of L's 29.4, M's 5.0, N's 65.0, E's 1.0 and B's of less than 1.0.

Figure 9A:
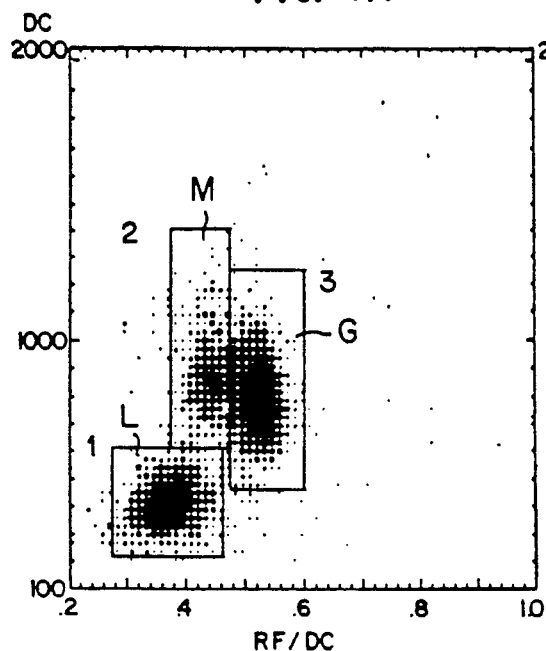
Figure 9B:
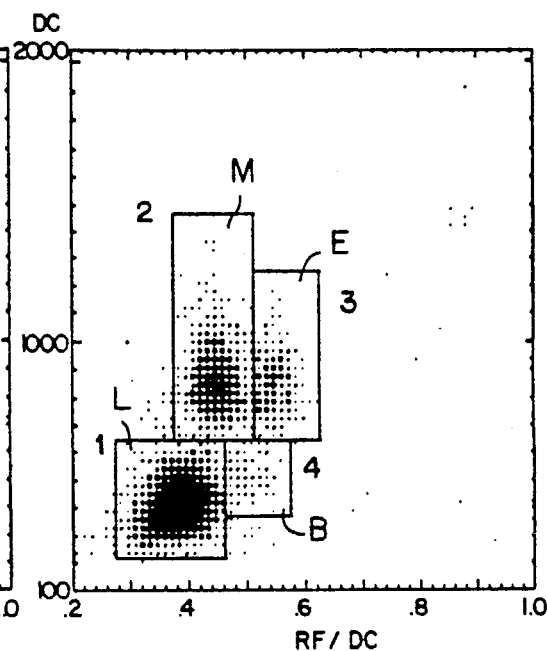

FIGS. 9A and 9B show scattergram results of a five-part WBC differential example similar to that of FIGS. 8A and 8B. A 20 microliter sample of whole blood analyzed in the same steps described with respect to FIGS. 8A and 8B resulting in the scattergram of FIG. 9A providing a count of L's 35.4 (1), M's 14.6 (2) and Gr's 50.0 (3). The scattergram of FIG. 9B provides a count of L's 66.4 (1), M's 25.0 (2), E's 6.6 (3) and B's 2.0 (4). The resulting five-part WBC differential results in counts of 35.4 L's, 14.6 M's, 45.5 N's, 3.5 E's and 1.1 B's was compared to a microscope count of 36 L's, 11 M's, 49 N's, 3 E's and 1 B.

Figure 10A:
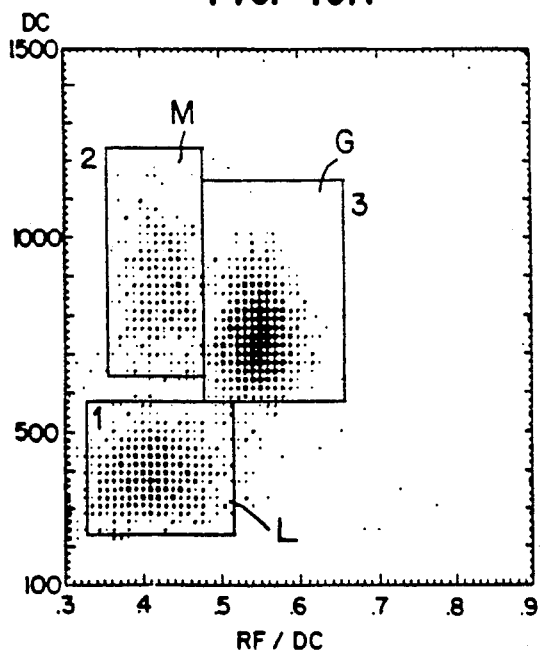
Figure 10B:
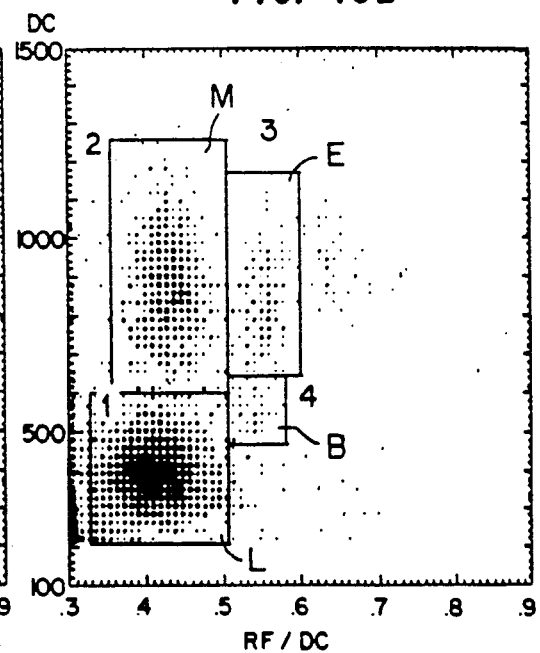

FIGS. 10A and 10B show scattergram results of a five-part WBC differential again similar to that of FIGS. 8A, 8B and 9A, 9B, however, in this example, lyse was utilized. In this example, 20 microliters of whole blood was combined with 80 microliters of buffer and 240 microliters of the RBC preferential lyse above referenced. The mixture is mixed for 6 seconds and then a quench is added. The time period is significant, because the lyse left unquenched for a period of time greater than about 10 seconds will start to affect the significant properties of the WBC's. The mixture with the RBC's removed is analyzed to provide the scattergram of FIG. 10A resulting in counts of L's 25.7 (1), M's 9.6 (2) and Gr's 65.0 (3).

A second portion of the mixture including a second 20 microliter sample of the whole blood is combined with 120 microliters of buffer and 10 microliters of magnetic microspheres with the N specific antibody bound thereto and mixed for 30 seconds and then placed in a magnetic field for 10 seconds. The RBC preferential lyse then is added to the N removed mixture with then is mixed for 6 seconds before it is quenched. The resulting scattergram FIG. 10B results in percentage counts of L's 74.6 (1), M's 21.6 (2), E's 2.9 (3) and B's 0.8 (4). The resulting five-part WBC differential results in percentage counts of L's 25.6, M's 9.6, N's 63.5, E's 1.06 and B's 0.3. Again a microscope comparison resulted in counts of L's 29.4, M's 5.0, N's 65.0, E's 1.0 and B's of less than 1.

Another example of scattergram results of a five-part WBC differential similar to that of FIGS. 10A and 10B is illustrated in FIGS. 11A and 11B. A sample of whole blood had two samples simultaneously analyzed in the same steps described with a respect to FIGS. 10A and 10B. The scattergram of FIG. 11A provides a count of L's 31.9 (1), M's 17.6 (2) and Gr's 50.4 (3). The scattergram of FIG. 11B provides a count of L's 67.1 (1), M's 24.1 (2), E's 7.6 (3) and B's 1.2 (4). The resulting five-part WBC differential results in counts of 31.9 L's, 11.4 M×s, 46.0 N's, 3.6 E's and 0.7 B's as compared to a microscope count of 36 L's, 11 M's, 49 N's, 3 E's and 1 B's.

A yet still further embodiment of a cell population analyzing method and apparatus embodying the parent application is designated generally by the reference numeral 292 in FIG. 12. The analyzer 292 includes a biological sample 294, again including at least a first set of viable biological cells and including a buffer if desired.

The sample 294 is combined via a line 296 with at least one reactant 298 via a line 300. In the analyzer 292, the RBC's are removed and the N's are shifted sequentially or simultaneously in a functionally designated station 302. The RBC remove function is designated 304 and the N move or shift portion is designated 306 to indicate that the functions can be performed simultaneously or sequentially. The RBC's can be removed magnetically or with lyse or with a combination of the two as previously described. The N's are removed or shifted by adding microspheres having an N specific antibody bound thereto to the mixture.

Once the RBC's are removed and the N's are moved or shifted, then the resulting mixture is fed via a line 308 to an analyzer 310. In this case, the N's are shifted sufficiently from the patterns of the E's and B's that a five-part WBC differential of M's, L's, E's, B's and N's is directly obtained. The functions of the analyze 292 can be performed on either of the instruments 56 and 210 or minor variations thereof.

The scattergram results of one example of a direct five-part WBC differential in accordance with the analyzer 292 is illustrated in FIG. 13. In this example, the biological sample 294 is 20 microliters of a whole blood sample and the reactant 298 is 10 microliters of non-magnetic microspheres with the N specific antibody bound thereto combined with 100 microliters of buffer and mixed in the substation 306 for 30 seconds. The RBC preferential lyse, 10 microliters thereof, then is added to the mixture which is mixed in the substation 304 for 6 seconds after which the quench is added. The RBC removed and N shifted mixture then is analyzed by the analyzer 310 resulting in the scattergram of FIG. 13 which provides a direct count of 29.6 L's, 13.6 M's, 52.2 N's, 3.4 E's and 1.06 B's as compared to a microscope determination of 35 L's, 5 M's, 56 N's, 4 E's and no B's. In this particular example, the whole blood sample was also analyzed on a general cell counting instrument of Coulter Electronics, Inc., which resulted in 29 L's, 11. M's and 59.9 Gr's (N's, E's and B's).

Referring now to FIGS. 14–26D, the embodiments of the present invention are illustrated.

Figure 14:
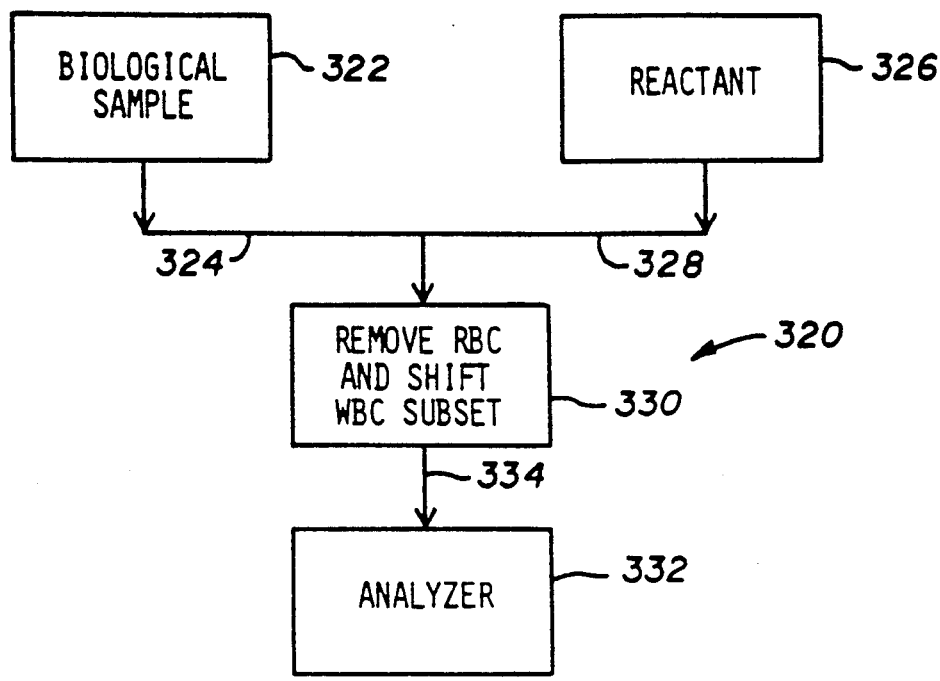

Referring to FIG. 14, a first embodiment of a WBC population subset analyzer method and apparatus is designated generally by the reference numeral 320. The analyzer 320 includes a biological sample 322, which contains at least a first set of viable biological cells (not illustrated), including at least one white blood cell population having at least one definable subset, such as in or from a whole blood sample. As utilized herein, WBC subsets are subsets of a WBC population to which specific monoclonal antibodies can be bound. A nomenclature now has been defined for the monoclonal antibodies by the World Health Organization and the International Immunology Society. The monoclonal antibodies are defined by a cluster of differentiation (CD) nomenclature which defines a particular specificity for a cell or group of cells and the monoclonal antibodies specific for that CD group. For example purpose only, four CD groups have been utilized in the following examples, CD4, CD8, CD2 and CD20. The CD nomenclature, specificity and some commercial sources of monoclonal antibodies are illustrated in Table I.

TABLE I

| Cluster of Defferentiation | Antibody (Commercial Source)[b] | Specificity |
| --- | --- | --- |
| CD2 (gp 50)[a] | T11 (Coulter) OKT11 (Ortho); Leu5$_a$ (BD) | E Rossette Receptor |
| CD4 (gp 56) | T4 (Coulter) OKT4$_a$ (Ortho); Leu3$_a$ (BD) | Helper/inducer T |
| CD8 (gp 32-33) | T8 (Coulter) OKT8 (Ortho); Leu2$_a$ (BD) | Cytotoxic/ Suppressor T |
| CD20 (gp 35) | B1 (Coulter) Leu 16 (BD) | All B cells except for plasma cells. B cell tumors, except |

TABLE I-continued

| Cluster of Defferentiation | Antibody (Commercial Source)[b] | Specificity |
| --- | --- | --- |
| | | for myeloma, some non-T ALL cells |

[a]gp — glycoprotein. molecular weight in kilodaltons
[b]Coulter — Coulter Immunology Division of Coulter Corporation (Hialeah, Florida)
BD — Becton-Dickinson Immunocytometry Systems (Mountain View, California)
Ortho — Ortho Diagnostic Systems (Raritan, New Jersey)

The cells of the biological sample 322 are to be involved in a biological reaction in a quantitative and/or qualitative determination or analysis. The sample 322 can include a buffer into which the cells are added.

The sample 322 is combined via a line 324 with at least one reactant 326 via a line 328. In the analyzer 320, the RBC's are removed from the mixture and simultaneously or sequentially at least one characteristic or at least one WBC subset is changed or shifted by a functionally designated RBC removing and WBC subset shifting station 330. As stated in the parent application, the RBC's can be removed from the mixture by the station 330 in a number of ways, such as enumerated with respect to the station 20. Simultaneously or sequentially, in the same mixture portion, at least one WBC subset is bound to WBC microspheres having monoclonal antibodies specific to the subset thereto to modify (change or shift) the resultant opacity and/or volume parameters of the cells.

The mixture with the RBC's removed and the WBC subset population shifted, then is fed to an analyzer 332 via a line 334. The analyzer 332 can be substantially identical to the analyzer 22. The WBC subset of interest generally is related as a percentage of the WBC population of interest. The analyzer 320 thus provides a fast direct analysis of at least one characteristic of a selected subset of a WBC population. The analyzer 320 can be utilized where the shifted WBC subset is not obscured by other more numerous cells, or where the number of the shifted cells of the WBC subset is a sufficient percentage as to be identifiable, even though obscured.

Figure 15:
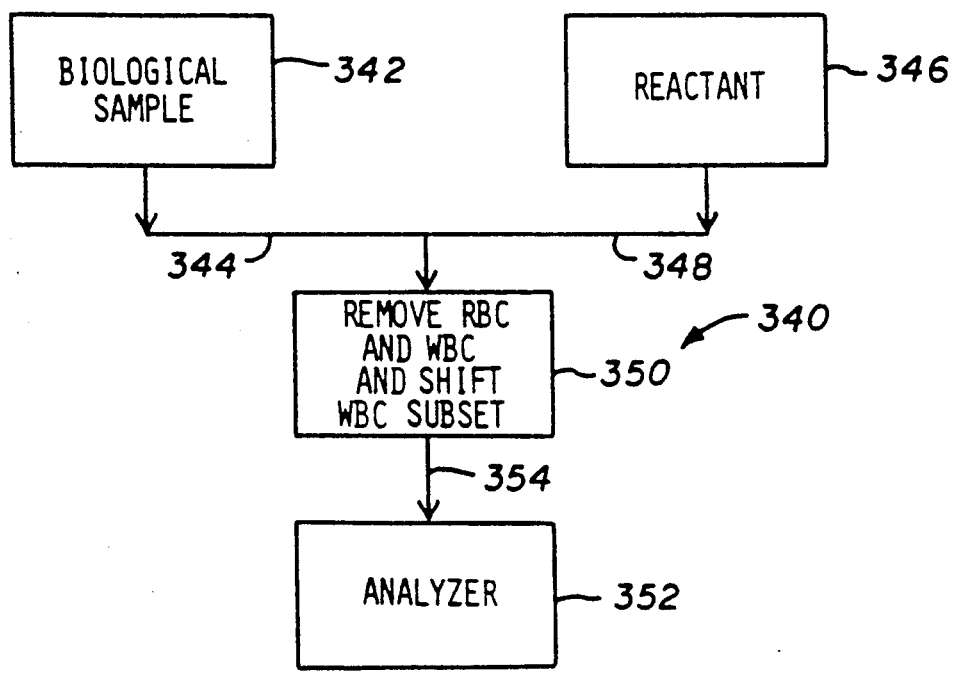

Referring to FIG. 15, a second embodiment of a WBC population subset analyzing method and apparatus is designated generally by the reference numeral 340. The analyzer 340 includes a biological sample, which contains at least a first set of viable biological cells (not illustrated), including at least one white blood cell population having at least one subset, such as in or from a whole blood sample. The cells of the biological sample 342 again are to be involved in a biological reaction in a quantitative and/or qualitative determination or analysis. The sample 342 can include a buffer into which the cells are added.

The sample 342 is combined via a lien 344 with at least one reactant 346 via a line 348. In the analyzer 340, the RBC's are removed from the mixture and simultaneously or sequentially at least one characteristic of at least one WBC subset is changed or shifted by a functionally designated RBC removing and WBC subset shifting station 350. As previously stated, the RBC's can be removed from the mixture by the station 350 in a number of ways, such as enumerated with respect to the station 20. Again, simultaneously or sequentially, in the same mixture portion, at least one WBC subset is bound to microspheres to modify (change or shift) the resultant opacity and/or volume parameters of the cells.

At the same time or sequentially, at least one WBC population or subset is removed from the mixture. The WBC population or subset is removed so that the WBC subset of interest is not obscured by the population. This preferably is accomplished by magnetically removing the WBC population after they are bound to magnetic microspheres which include a monoclonal antibody bound thereto which is specific to the WBC population.

The mixture with the RBC's and the WBC population removed and the WBC subset populations shifted then is fed to an analyzer 352 via a line 354. The analyzer 352 again can be substantially identical to the analyzer 22.

Figure 16:
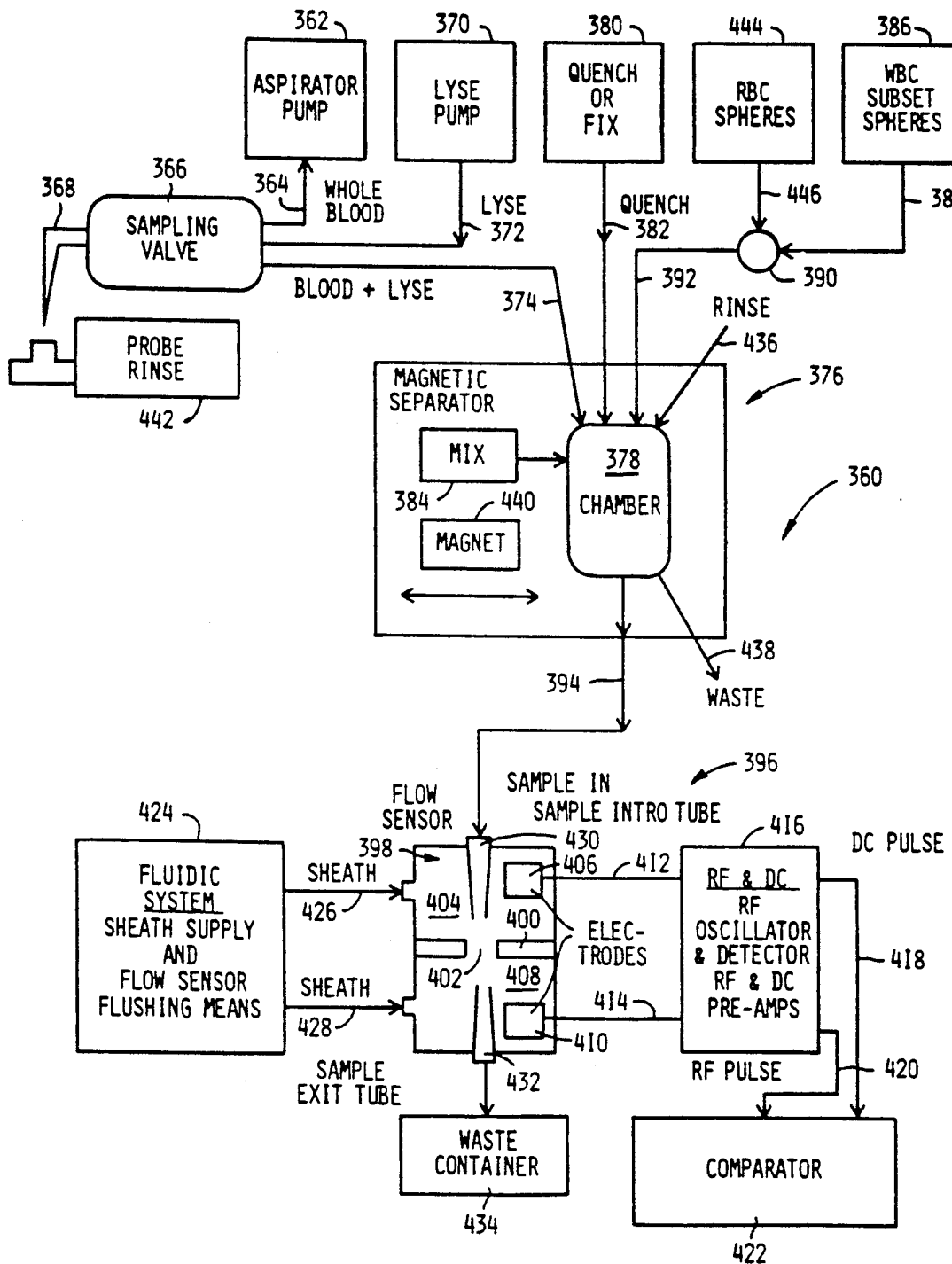

One specific embodiment of an analyzer instrument embodying the parent application and which can accomplish the analyzing methods of the first and second analyzers 320 and 340, is designated generally by the reference numeral 360 in FIG. 16.

In the instrument 360, like the instrument 56, only one specific enumeration is illustrated, which can be varied in almost endless detail in accordance with the principles of the parent application. Further, the instrument 360 is shown in generally functional detail and the specific embodiments can be structurally implemented in many known ways.

The instrument 360 includes an aspirator pumping mechanism 362 which is utilized to draw the biological sample of interest, for example the sample 322 or 342 into the instrument 360. The aspirator 362 is coupled via a line 364 to a sampling valve 366 which can be coupled to a sample probe 368. A lyse pump 370 can include the lyse, such as part of the reactant 326 or 346 and is also coupled to the valve 364 via a line 372. The valve 366 an the pump 362 can aspirate the biological sample 322 or 342 along with the lyse via the pump 370 when appropriate. Preferably, the biological sample 322 or 342 is added separately from the lyse.

The reactant mixture or the biological sample itself, then is fed via a discharge line 374 into a mixing apparatus 376. The mixer 376 includes a mixing chamber 378 into which the sample or reactant is fed. The analyzers 320 and 340 differ only slightly in operation and hence will be described together.

In operation, if the RBC's have been lysed by the lyse from the pump 370, then when the reaction is completed a quench or fix is supplied from a station 380 via a line 382. The RBC removal reaction then is completed. The reaction can be assisted by mixing the lyse and the sample in the chamber 378 as illustrated functionally at 384.

Either before, after or concurrently with the removal of the RBC's, the WBC's are shifted and in the case of the analyzer 340, one WBC population or subset also is removed. The WBC subset is shifted by adding the specific WBC microspheres from a station 386 via a line 388, a valve 390 and a chamber line 392. The WBC microspheres are mixed with the mixture or the sample by the mixing mechanism 384.

The details of an an appropriate mixing apparatus 376 can be substantially identical to the mixing apparatus 70. By utilizing the mixer 376 the reactions are greatly enhanced in speed without significantly damaging the properties of interest of the cells, such as, can occur by raising the reaction temperature. Further, the reactions generally are completed in significantly less than a few minutes and generally can be on the order of two minutes or less. This allows a rapid analysis of the automatic high volume analyzer instrument 360.

In the analyzer 320, the quenched reactant with the RBC's removed by the lyse (as from the station 20) and the modified WBC subset then is fed via a line 394 to a WBC analyzer 396 (i.e. analyzer 332). The analyzer 396 can be of many physical types in accordance with the counting and sizing techniques described by Wallace H. Coulter in U.S. Pat. No. 2,656,508 and embodied in the numerous commercial blood cell counter of the assignee, Coulter Electronics, Inc.

As previously described, the analyzer 396, in general, includes a flow sensor or sensing chamber 398. The chamber 398 includes a transducer 400 which has an aperture 402 therethrough. The chamber 398 includes a first portion 404 which has a first electrode 406 in contact with the fluid therein.

The chamber portion 404 and the electrode 406 communicate through the aperture 402 with a second chamber portion 408 having a second electrode 410 therein. The electrodes 406 and 410 are coupled via reactive leads 412 and 414 to an RF/DC source and sensing circuit 416. The circuit 416 couples both a DC, or low frequency current or signal, and a high frequency signal between the electrodes 406 and 410.

The low frequency signal is utilized to sense the amplitude of a signal pulse caused by a cell passing through the aperture 402. The high frequency signal is utilized to obtain the electrical opacity of the same cell passing through the aperture 402.

The measuring of the electrical opacity of cells was described by Wallace H. Coulter and Walter R. Hogg in U.S. Pat. No. 3,502,974 and several patents and publications of the assignee, Coulter Electronics, Inc., since that patent. One specific circuit which can be utilized herein is disclosed in U.S. Ser. No. 921,654, incorporated herein by reference.

The signals generated by the circuit 416 from the sensed cells are coupled via a DC signal lead 418 and an RF signal lead 420 to a comparator 422 (like the comparator 26).

The analyzer 396 can include a sheath flow to focus the cells in the sensor 398, in the well known manner. The sheath flow can be provided by a fluidic system 424, coupled to the sensor by a pair of lines 426 and 428 in a known manner. The sample reaction mixture an be fed into the sensor 398 via an introduction tube 430 and can be fed from the sensor 398 via an exit tube 432 into a waste container 434.

Following each operation, the mixer 378 is cleaned or flushed via a rinse line 436 and exhausted through a waste line 438. Once the chamber 378 is cleaned, another sample or sample portion can be fed into the instrument 360.

In the analyzer 340, the operation is the same as the analyzer 320 with the addition of magnetic white blood cell population or subset microspheres. The WBC subset bound thereto then are removed by a magnetic field during and/or after the mixing process by a magnetic field or magnet 440. The field can be provided by electromagnetic means or by the magnet 440 being physically moved with respect to the chamber 378 to capture the magnetically bound WBC subset. The mixture without the bound WBC subset then is fed via the line 394 tot he analyzer 396 in the manner previously described to obtain the analysis (like the analyzer 320).

The instrument 360 then is prepared to take the next sample for the next analysis. The probe 368 can be cleaned by a probe rinse mechanism 442 and the lines and chamber 378 can be flushed in a conventional manner. Each analysis of the succeeding sample mixture is obtained in a rapid and automatic fashion. The period between the analysis of succeeding sample mixtures can be on the order of five minutes or less.

Alternatively to the utilization of the lyse, in either of the analyzers 320 and 340, the sample 322 or 342 can be fed to the mixer 376 via the valve 366 without any lyse. In this case the RBC's can be removed magnetically by utilizing microspheres with the RBC specific antibody bound thereto from an RBC microsphere station 444 and fed to the valve 390 via a line 446 and hence to the chamber 376 via the line 392. Where no lyse is utilized, the bound RBC's also are magnetically removed by the magnet 440 after mixing in a manner substantially identical to the magnetically bound WBC's described above.

Further, in a second case to promote the speed or efficiency of the reaction, a reaction mixture of the sample with both the RBC lyse and with the RBC magnetic beads can be utilized. The reaction mixture is mixed, the lyse is quenched and the bound RBC's are magnetically removed and then the WBC's are analyzed as previously described.

Figure 17A:
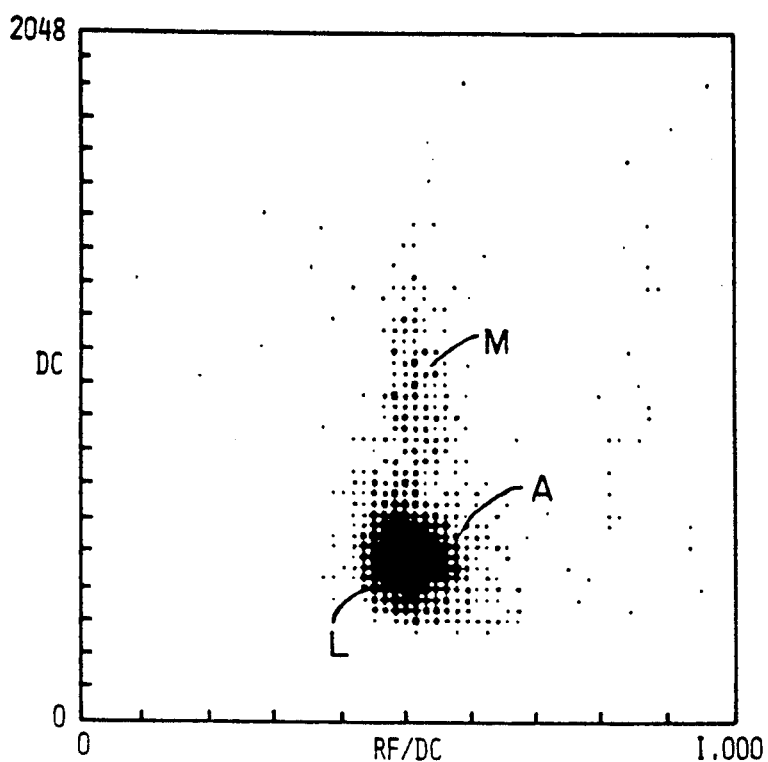
FIGS. 17A and 17B are a scattergram of one set of results utilizing a prototype analyzer system similar to that illustrated with respect to FIGS. 3 and 16.
Figure 17B:
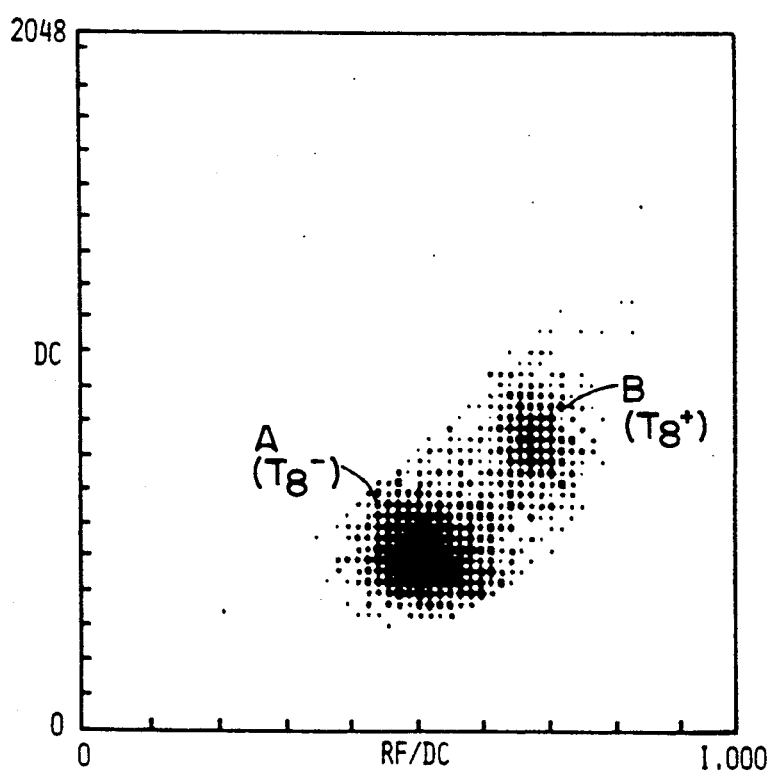

Referring now to FIGS. 17A and 17B, two sets of results depicted in scattergrams obtained from a whole blood sample utilizing a prototype analyzer similar tot he instrument 360 are illustrated. Two WBC populations are removed and the $T_8$ subset is directly analyzed. The $T_8$ subset is the cells or formed bodies which have the receptor or antigen to which the $T_8$ specific antibody binds to. In the Figures, these are designated as $T_8^+$. The cells are formed bodies which do not have the receptor or antigen to which the $T_8$ specific antibody binds to are designated as $T_8^-$. In these examples, the biological medium 342 was a 20 microliter sample of whole blood utilized with the mixer 376. In both FIGS. 17A and 17B, the 20 microliter sample of whole blood, medium 342, was combined with 40 microliters of magnetic microspheres with the RBC specific antibody bound thereto, combined with 120 microliters of buffer solution and 10 microliters of magnetic microspheres with an N and E specific antibody bound thereto, combined with 30 microliters of buffer solution which together form the reactant 346. One such exemplary N and E specific antibody is disclosed in U.S. Ser. No. 068,618, entitled MONOCLONAL ANTIBODY SPECIFIC TO A COMMON DETERMINANT SITE OF NEUTROPHILS AND EOSINOPHILS, filed Jun. 3, 1987, now U.S. Pat. No. 4,865,971, which is incorporated herein by reference.

The magnetic microspheres can be of any suitable type and in the example are polystyrene magnetic microspheres of 0.7 micron diameter, with a weight to volume of 10% solids, sold by Seradyn, Inc. of Indianapolis, Ind. The reaction mixture then was mixed in the mixer 376 for 10 seconds, placed in the magnetic field of the magnet 440 for 15 seconds and then the resulting mixture with the RBC's, E's and N's removed was analyzed in the analyzer 396. The resulting scattergram A is illustrated in FIG. 17A.

The scattergram of FIG. 17B results from the same procedure with the addition of 12.5 microliters of non-magnetic microspheres with a $T_8$ specific antibody bound thereto combined with 12.5 microliters of buffer solution to form the reactant 346. The $T_8$ specific antibody is sold under the Trademark COULTER CLONE ® by Coulter Immunology Division of Coulter Corporation. The non-magnetic microspheres again can be of any suitable type and in the examples are surfactant free sulfated polystyrene latex microspheres of 1.78 micron diameter with a weight to volume of 8% solids, sold as IDC microspheres by Intefacial Dynamics of Portland, Ore.

The addition of the $T_8$ microspheres shifts the bound CD8 cells to an area B where they separately can be identified and counted as seen by comparing the scattergram of FIGS. 17A and 17B. In FIG. 17A the CD8 cells are hidden by the remaining WBC's. The N's and E's are removed from the scattergrams or they would obscure the identification of the shifted CD8 cells in FIG. 17B. FIG. 17A illustrates the removal of the N's and E's, while FIG. 17B then clearly illustrates the shift of the DC 8 bound cells from area A to area B. The buffer solution can be phosphate buffered saline sold by Sigma Chemical Company of St. Louis, Miss.

Figure 18A:
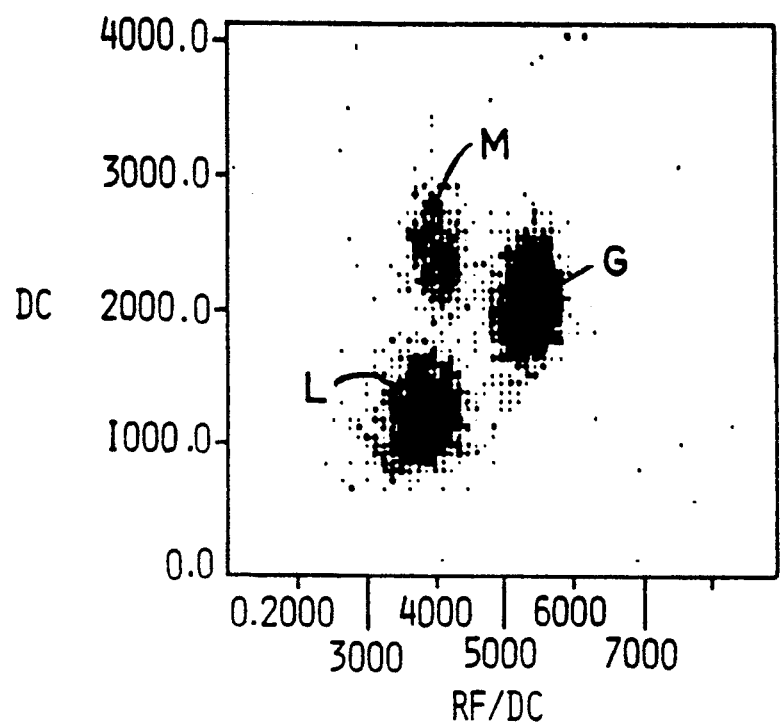
FIG. 18A is a scattergram of the L, M and G populations
Figure 18B:
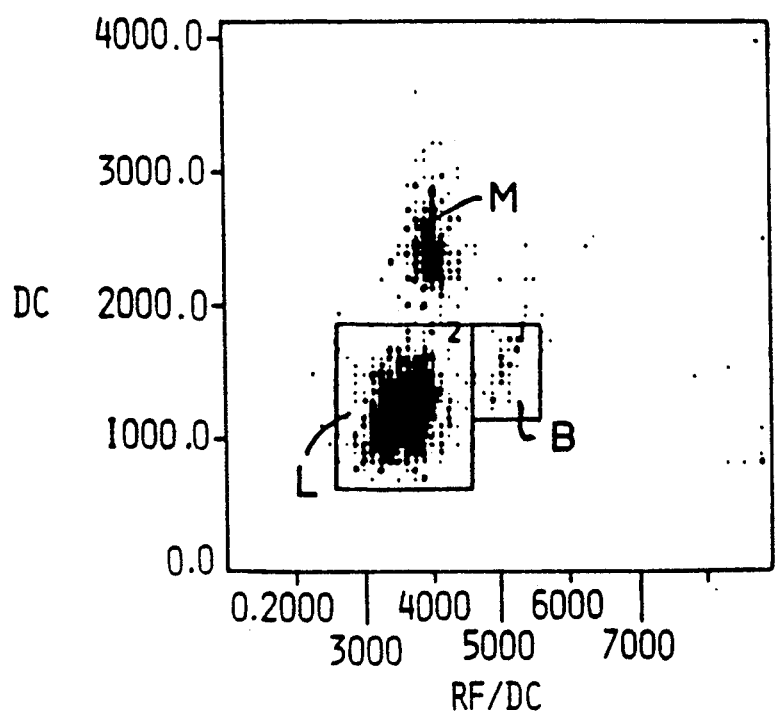
FIG. 18B is a scattergram of the L, M and B populations utilizing a prototype analyzer system similar to that illustrated with respect to FIG. 16.
Figure 19A:
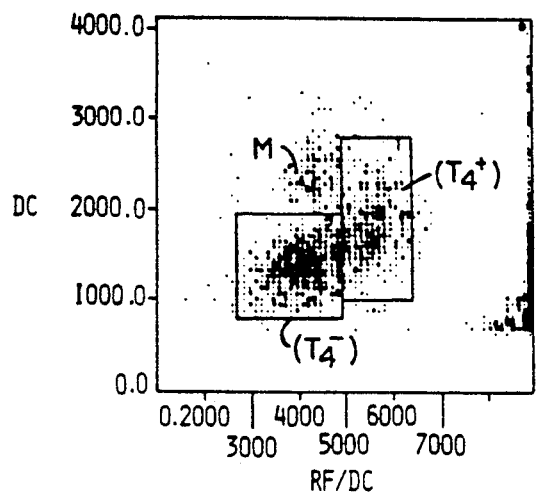
Figure 19B:
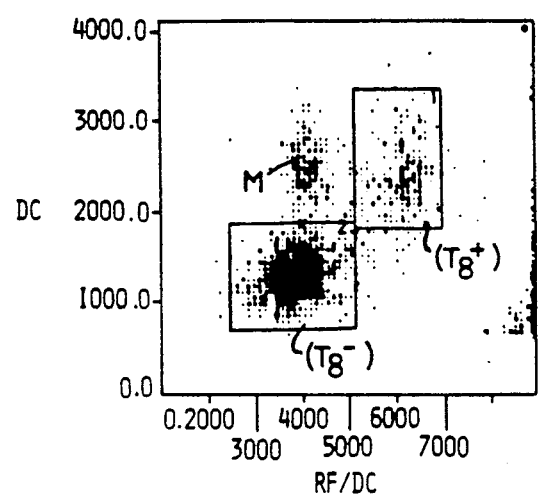
Figure 19C:
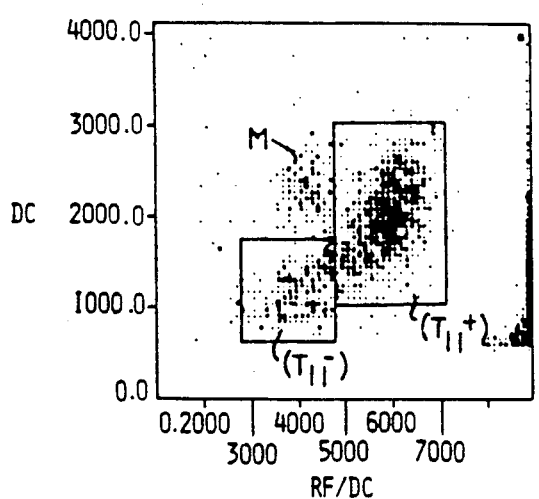
Figure 19D:
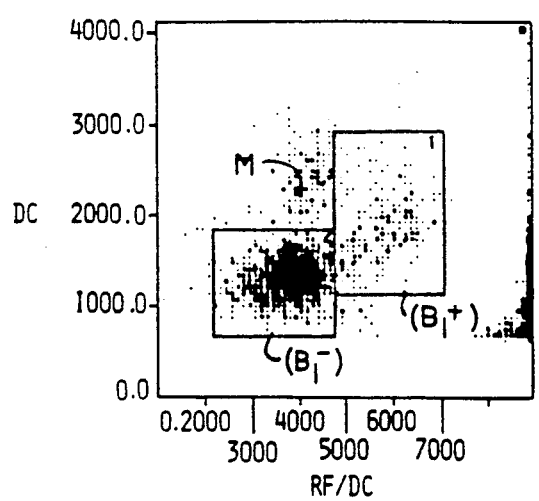
Figure 20A:
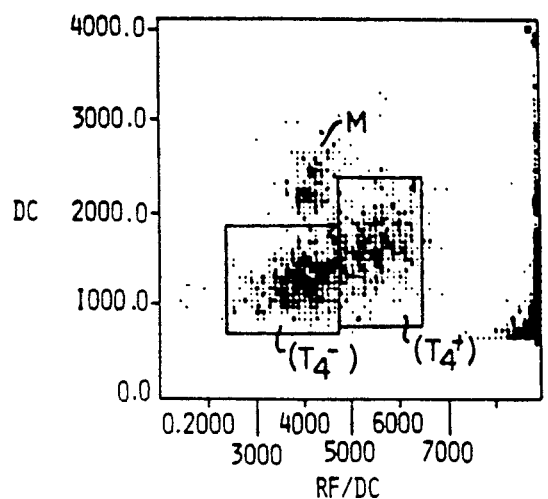
Figure 20B:
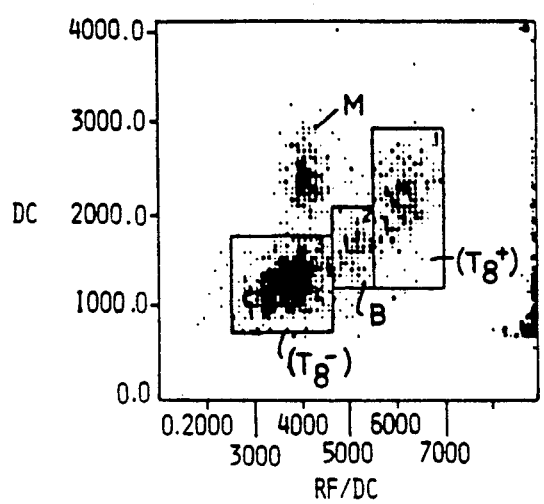
Figure 20C:
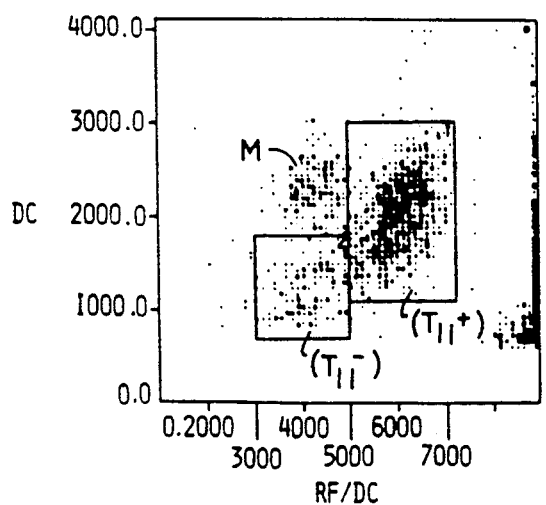
Figure 20D:
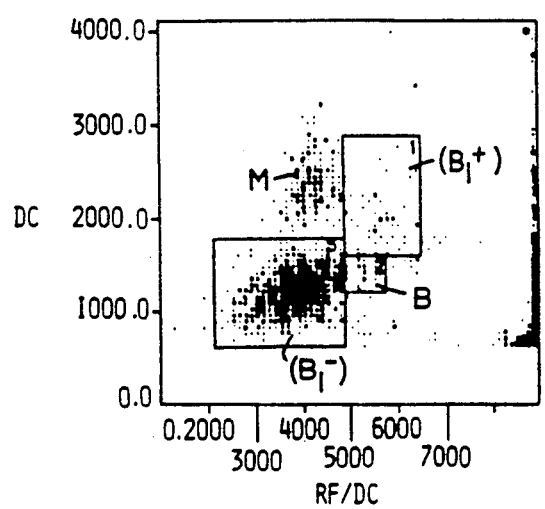
Figure 21A:
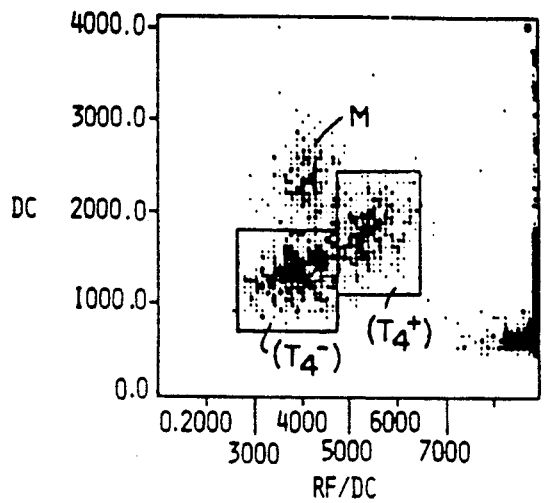
Figure 21B:
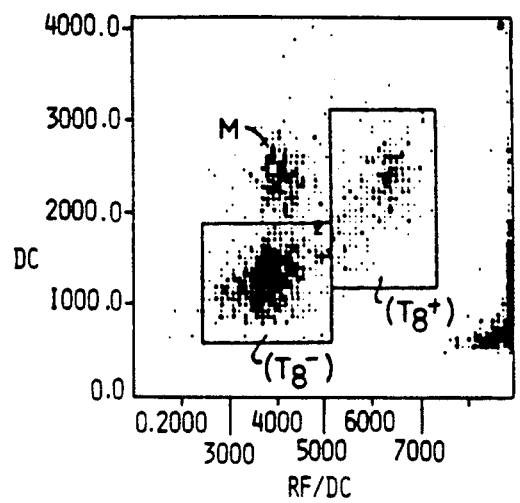
Figure 21C:
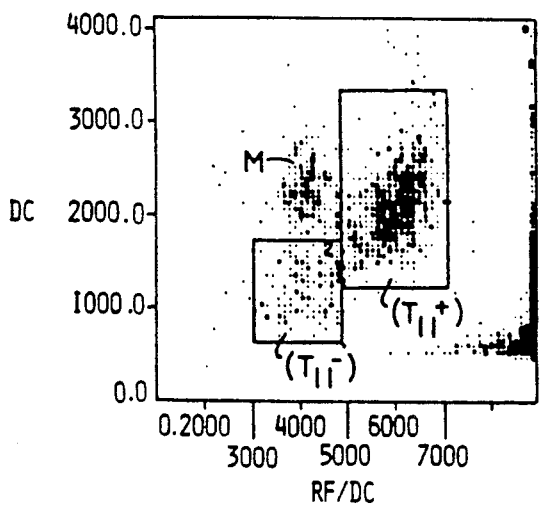
Figure 21D:
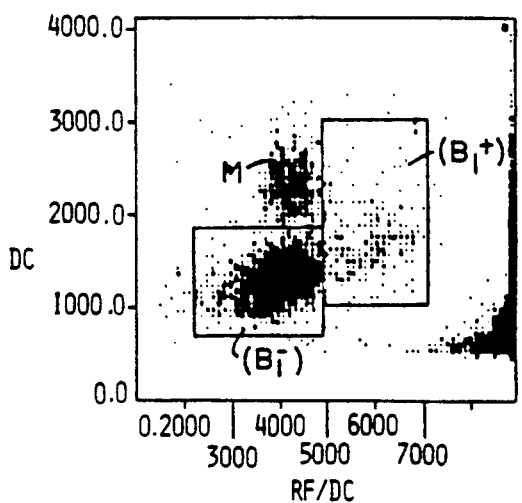

FIG. 18A further illustrates the normal scattergram or 3 parameter histogram positioning of the M, L and G cell populations from the analyzer 352. Without removal of the G's, as seen in FIG. 17B, the area B of the shifted WBC subset would be obscured by the G's, which are far more numerous in number. FIG. 18B is a scattergram illustrating the WBC populations M, L and B remaining after removal of the E's and N's. Although the B's still may partially obscure the area of interest, their percentage number of the WBC populations is of a small enough order to not substantially affect the desired calculation of the subset, percentage. However, the B's contribution can be subtracted from the subset percentage if so desired.

Referring now to FIGS. 19A-D, 20A-D and 21A-D, the direct subset analysis of the CD2, CD4, CD8 and CD20 WBC subset populations of respective samples from three different patients is illustrated. In the case of each subset population, 28 microliters of a whole blood sample was combined with 20 microliters of magnetic microspheres (2.5% weight per volume solution) with the N and E specific antibody bound thereto. In addition, non-magnetic microspheres with the respective monoclonal antibody for the respective WBC subset are also combined with the sample. The respective amounts of $T_4$, $T_8$, $T_{11}$ or $B_1$ coated microspheres are 40 microliters each. (1% weight per volume solution for each one). Each respective total mixture, i.e. N and E microspheres with $T_8$, for example, is combined with a buffer solution of phosphate buffered saline, 1% bovine serum albumin, pH of 7.2 to 7.4 for a total volume of 150 microliters. Each respective mixture is mixed in the chamber 378 by the mixer 376 for two minutes and then placed in the magnetic field 440 for one minute. In these examples, the RBC's are removed sequentially utilizing the lyse above referred to. The WBC microspheres are first added, then the RBC's are removed by lysing with 300 microliters of lyse, such as Erythrolyse lytic reagent sold by Coulter Electronics, such as from the lyse source 370. The mixture then is quenched with 120 microliters of quench, such as Stabilyse, a leukocyte preservative also sold by Coulter Electronics, from the source 380 and then fed to the analyzer 396 for analysis.

The right-hand block (1) in each scattergram represents the respective WBC subset population of interest. The blocks 1, 2, 3, etc. illustrated in the Figs. are visually or automatically fit around the WBC population or subset of interest.

The results were compared utilizing conventional flow cytometry and gave the following comparative results in percentages for the three samples by the method of the invention (SHIFT) vs. flow cytometry (CYT).

|  | Shift | CYT | Shift | CYT | Shift | CYT | Shift | CYT |
|---|---|---|---|---|---|---|---|---|
|  | $T_4$ (FIG. 19A) | | $T_8$ (FIG. 19B) | | $T_{11}$ (FIG. 19C) | | $B_{11}$ (FIG. 19D) | |
| Patient Sample 1 | 51 | 52 | 18 | 22 | 82 | 76 | 15 | 13 |
|  | $T_4$ (FIG. 20A) | | $T_8$ (FIG. 20B) | | $T_{11}$ (FIG. 20C) | | $B_1$ (FIG. 20D) | |
| Patient Sample 2 | 53 | 54 | 32 | 29 | 89 | 83 | 6.5 | 7.5 |
|  | $T_4$ (FIG. 21A) | | $T_8$ (FIG. 21B) | | $T_{11}$ (FIG. 21C) | | $B_1$ (FIG. 21D) | |
| Patient Sample 3 | 46 | 46 | 24 | 18 | 86 | 81 | 11 | 10 |

Figure 22A:
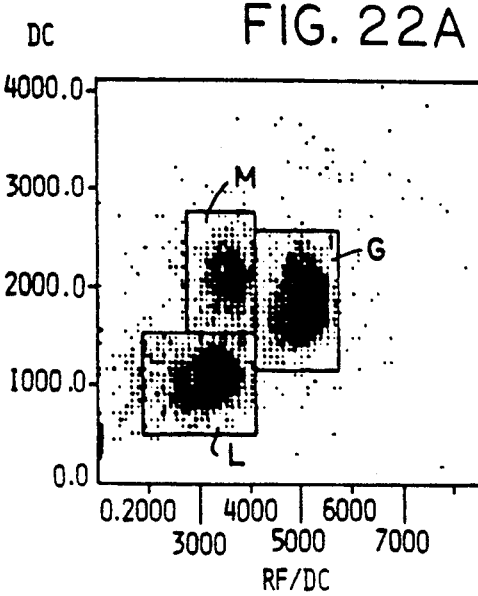
FIG. 22A is a scattergram similar to the scattergram of FIG. 18A.
Figure 22B:
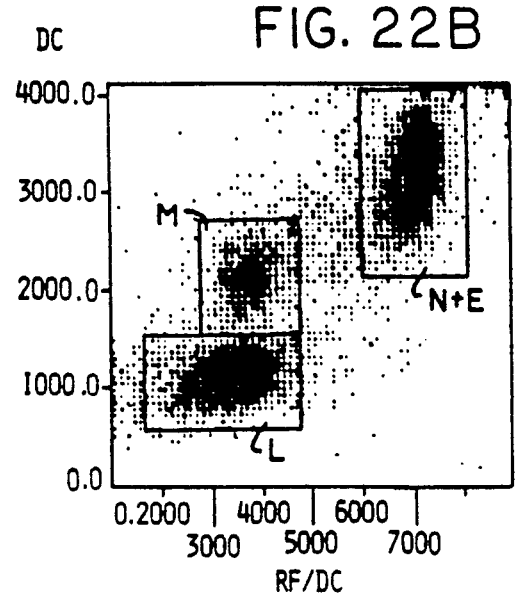
FIG. 22B is a scattergram illustrating shifting of the E and N populations and FIG. 22C is a scattergram illustrating shifting of the E, N and CD4 populations.
Figure 22C:
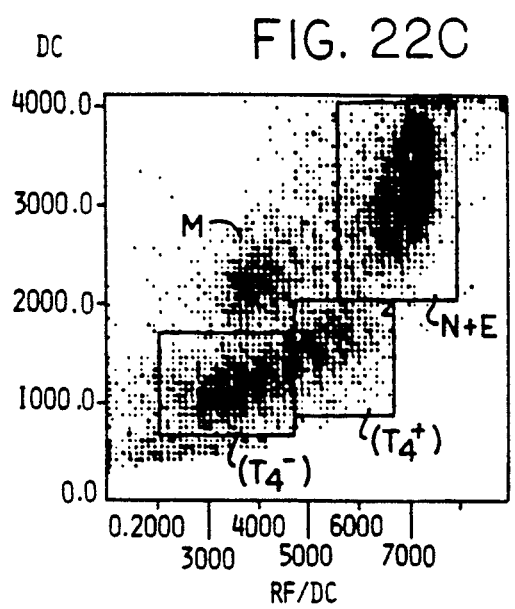

FIG. 22A also illustrates the normal scattergram or 3 parameter positioning of the M, L and G cell populations from the analyzer 352. Without removal of the N's and E's, the CD4 cell population would be obscured. By shifting the N's and E's with the N and E specific monoclonal antibody microspheres to an area or block 1 illustrated in FIG. 22B, the CD4 population can be shifted and viewed in the block or area 2. This area would have been obscured by the N's and E's as seen in FIG. 22A. In this example for FIG. 22C, 28 microliters of a whole blood sample were combined with 50 microliters of 2.2 micron microspheres with the N and E specific monoclonal antibody bound thereto and 50 microliters of microspheres with $T_4$ specific monoclonal antibody bound thereto and 22 microliters of diluent. FIG. 22B was the same without the $T_4$ microspheres and with 72 microliters of diluent and FIG. 22A was the same without any microspheres and 122 microliters of diluent.

Figure 23A:
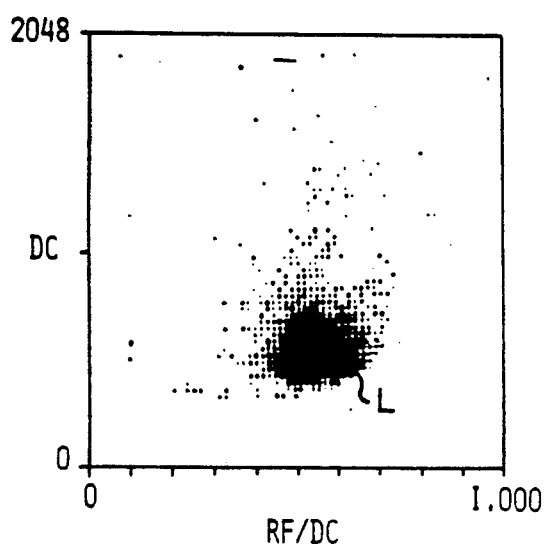
FIGS. 23A-D are scattergrams illustrating a direct WBC subset analysis utilizing one microsphere bound to the WBC subset of interest and a second microsphere bound to the first microsphere.
Figure 23B:
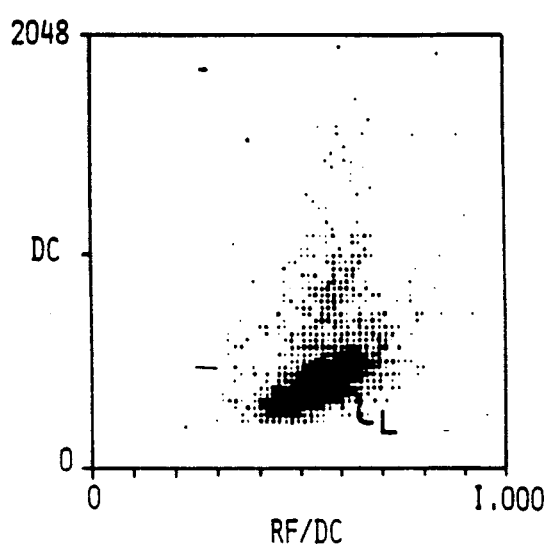
Figure 23C:
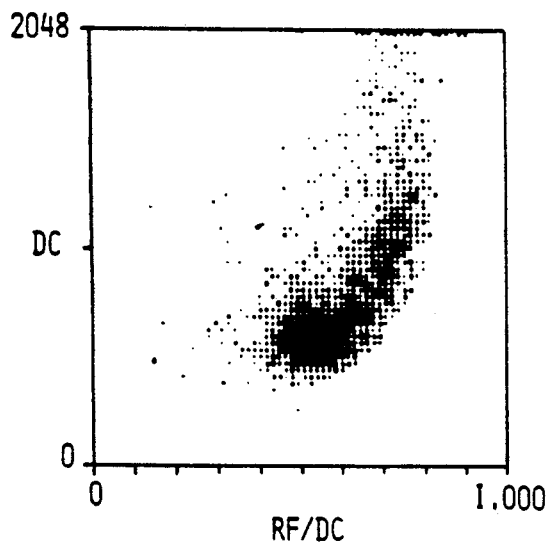
Figure 23D:
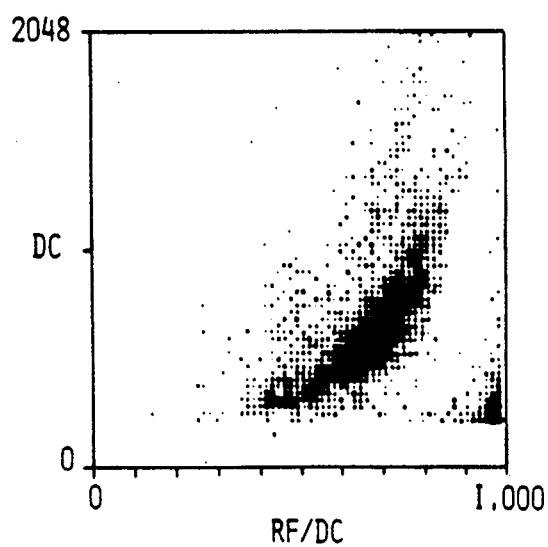

Referring to FIGS. 23A-D, direct WBC analysis utilizing a plurality of microspheres bound to the WBC subset of interest is illustrated. FIGS. 23A and 23B respectively illustrate scattergrams of only the L population with the $T_4$ WBC subset and the $T_{11}$ WBC subset each shifted with 0.8 micron non-magnetic microspheres. The shift is insufficient to differentiate the WBC subset population in FIGS. 23A and 23B. FIGS. 23C and 23D respectively illustrate scattergrams of only the L population with the $T_4$ WBC subset and the $T_{11}$ WBC subset shifted by being bound to both a 0.8 micron and a 2.2 micron microsphere. The 2.2 micron microsphere is bound to the 0.8 micron microsphere by having Goat anti-mouse IgG antibody bound thereto, which binds to the $T_4$ or $T_{11}$ antibody bound to the 0.8 micron microsphere.

Figure 24A:
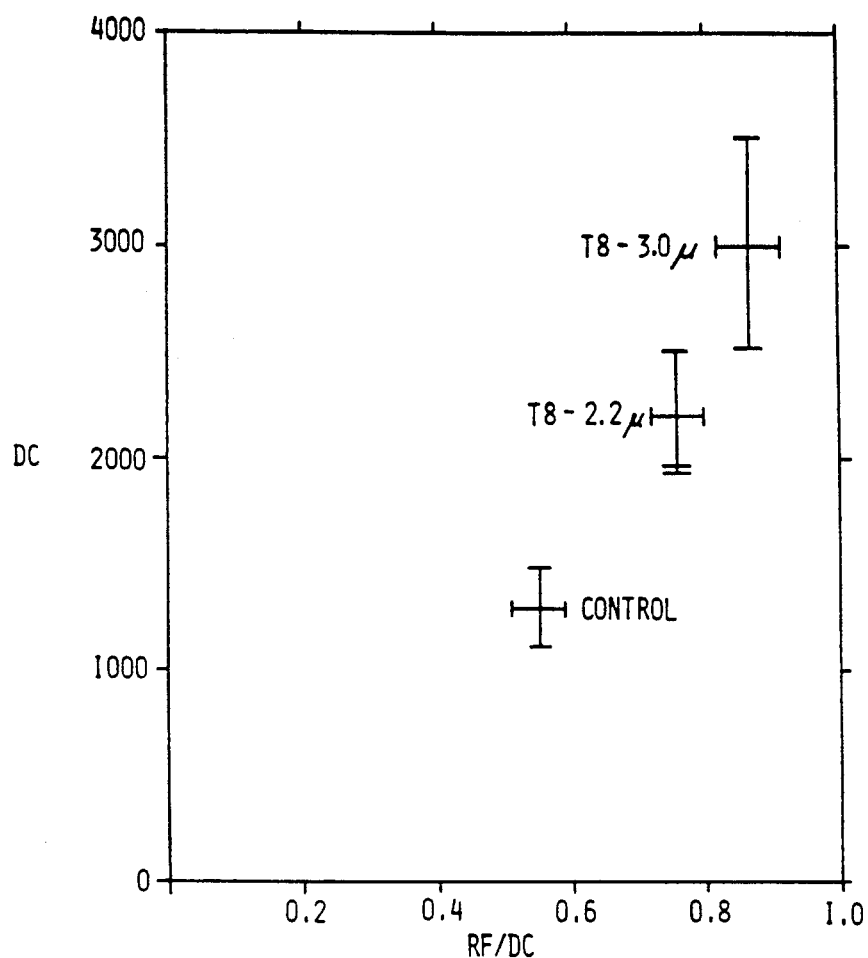
FIGS. 24A-C are scattergrams illustrating the effect of the size of the microsphere utilized in the shifting analysis of the invention.
Figure 24B:
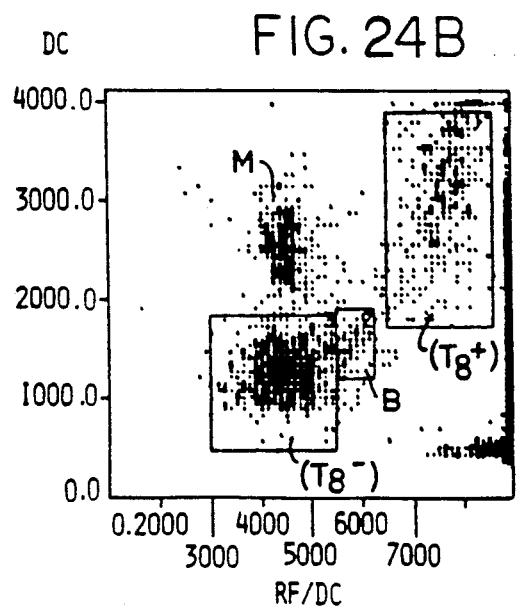
Figure 24C:
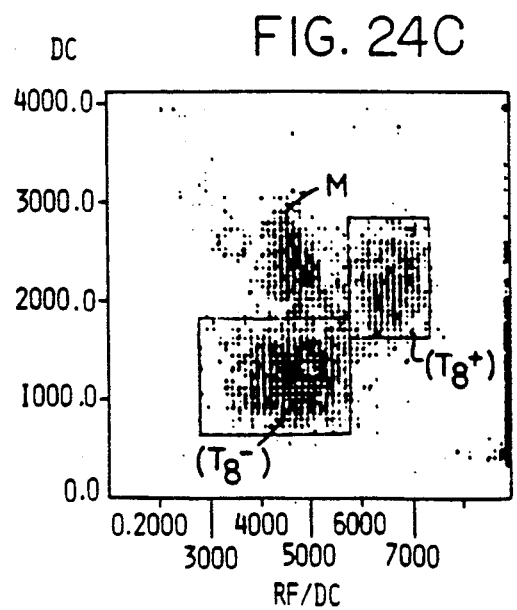

The effect of the size of the non-magnetic microsphere bound to the WBC subset of interest is illustrated in FIGS. 24A-C. In this example, a 28 microliter sample of whole blood was combined with 10 microliters of magnetic microspheres having the N and E specific antibody bound thereto (2.5% weight per volume solution) and 40 microliters of non-magnetic microspheres having the $T_8$ specific antibody bound thereto (1% weight per volume solution). The $T_8$ microspheres were of two different sizes to illustrate the difference in the shift on the scattergram. A buffer solution again was added to form a mixture volume of 150 microliters. The mixture was mixed for 2 minutes and placed in the magnetic field for 1 minute. The resultant N and E removed mixture then was lysed to remove the RBC and the analyzed. FIG. 24A illustrates a control WBC subset without a microsphere attached thereto, a $T_8$ WBC subset with a 2.2 micron non-magnetic microsphere bound thereto and a $T_8$ WBC subset with a 3.0 micron non-magnetic microsphere bound thereto. The width and height illustrate the standard deviation of the detected signal. FIG. 24B is a scattergram illustrating the $T_8$ WBC subset shift with the 3.0 micron microspheres bound thereto, while FIG. 24C is a scattergram illustrating the $T_8$ WBC subset shift with the 2.2 micron microspheres bound thereto. The analyzed percentage of the $T_8$ WBC subset for the different microspheres were respectively, 20.9 and 19.3. The larger microsphere clearly generated a more distinct scattergram pattern as illustrated by FIG. 24B.

Figure 25A:
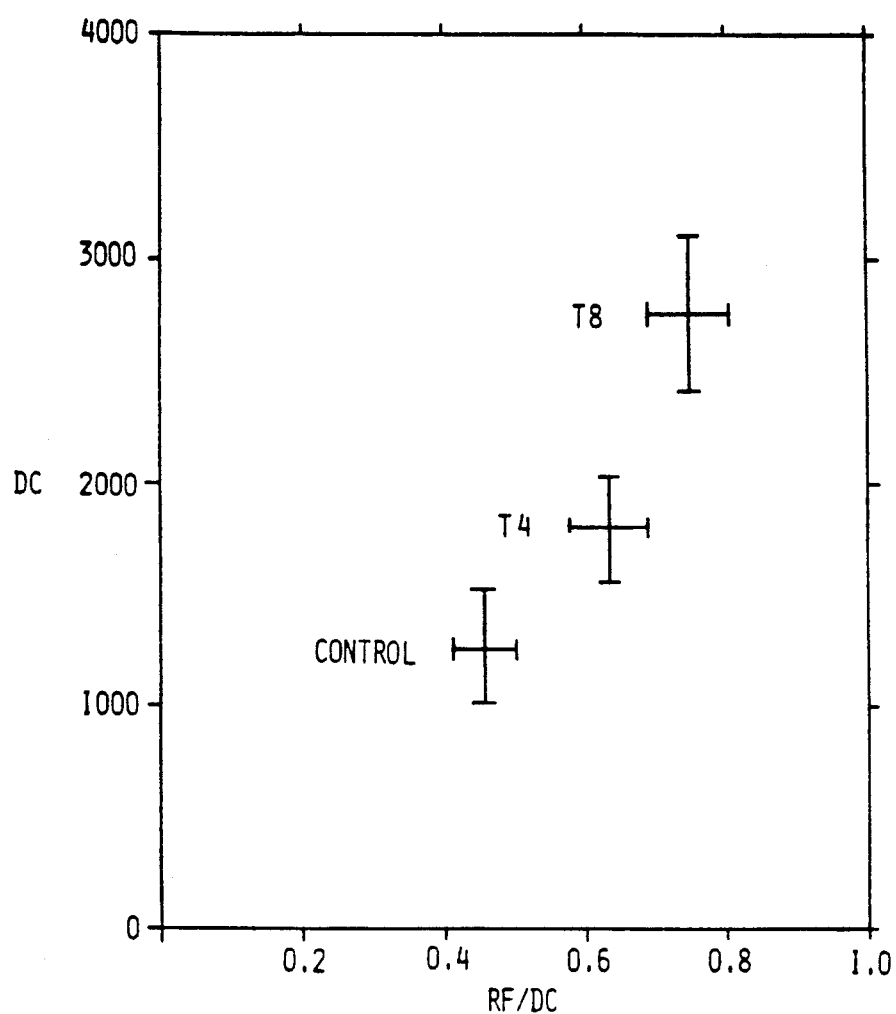
FIGS. 25A-D are scattergrams illustrating a simultaneous analysis of two WBC subset populations by the techniques of the invention.
Figure 25B:
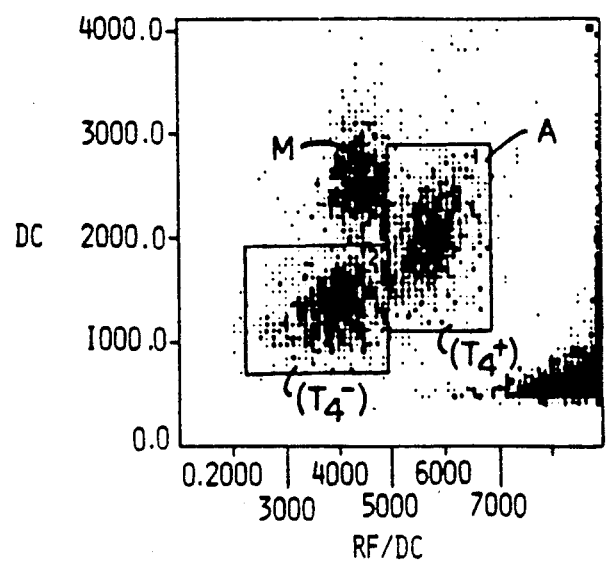
Figure 25C:
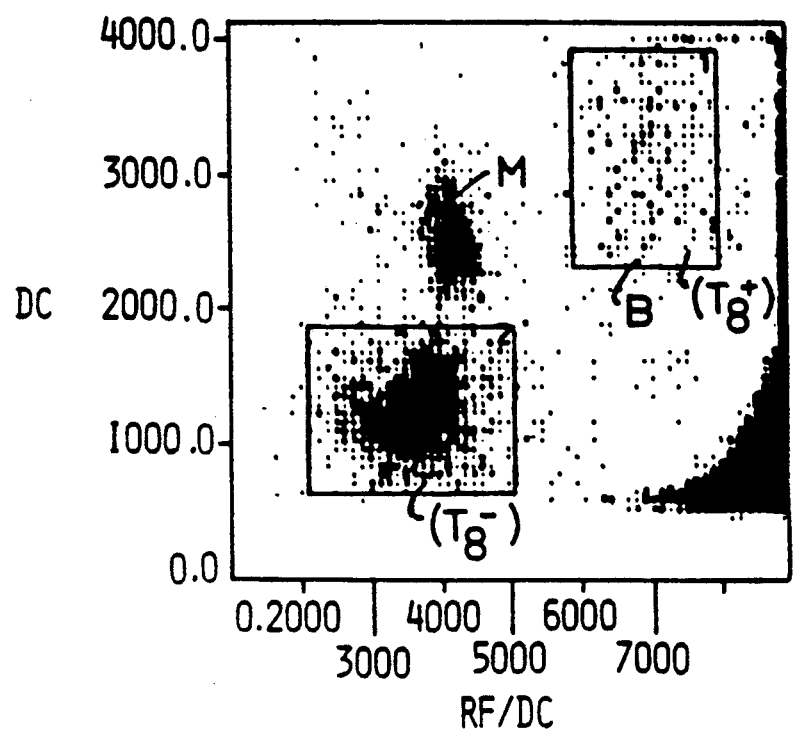
Figure 25D:
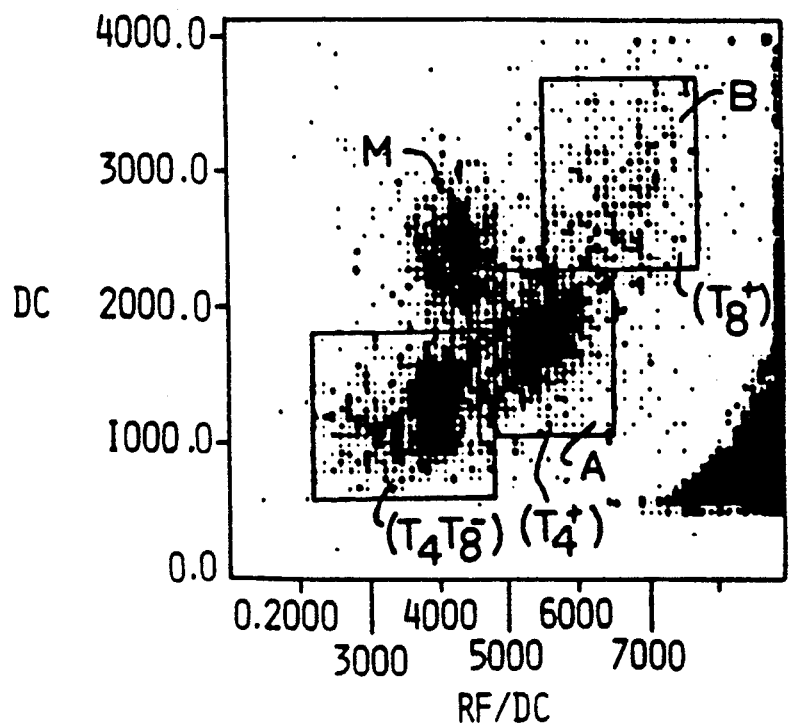

Referring now to FIGS. 25A-D, the simultaneous direct analysis of two WBC subset populations is illustrated in accordance with the invention. In this example, 28 microliters of a whole blood sample was combined with 10 microliters of magnetic microspheres having the N and E specific antibody bound thereto, 52 microliters of buffer solution and 40 microliters of non-magnetic 3.0 micron microspheres with the $T_8$ specific antibody bound thereto and mixed for 2 minutes. The mixture then was placed in the magnetic field for 1 minute and then the resultant N and E removed mixture was lysed to remove the RBC and then analyzed. FIG. 25A illustrates a control WBC subset sample without a microsphere bound thereto, a $T_4$ reading with a 2.2 micron non-magnetic microsphere bound thereto and a $T_8$ reading with a 3.0 micron non-magnetic microsphere bound thereto. This illustrates the separation between the two shifted WBC subset populations. FIG. 25B is a scattergram analysis with only the $T_4$ WBC subset population bound to the 2.2 micron microspheres shifted to area A and FIG. 25C is a scattergram analysis with only the $T_8$ WBC subset population bound to the 3.0 micron microspheres shifted to area B. FIG. 25D illustrates a scattergram analysis with both the $T_4$ and $T_8$ WBC subset populations shifted to the respective areas A and B. This allows a simultaneous analysis of both the $T_4$ and $T_8$ subset populations.

Referring now to FIGS. 26A-D, three populations of L's, M's and G's are illustrated on four different scattergrams utilizing different parameters. Although the previous examples have been illustrated utilizing DC vs. opacity (RF/DC), the scattergrams can be formed utilizing virtually any two different parameters. FIG. 26A illustrates a scattergram utilizing DC vs. RF along, FIG. 26B utilizes RF vs. opacity, FIG. 26C utilizes DC-RF vs. opacity and FIG. 26D utilizes DC vs. opacity as previously illustrated. Further, although DC vs. RF or RF/DC has been utilized, any two different frequencies are adequate as long as the signals are separable from each other, because of their frequency spectrum location and/or the difference in phase relationship. Opacity is a preferably parameter since it essentially is a normalization of the RF signal. Clearly, as illustrated in FIGS. 26A-D, the presentation of the data can be varied as desired. DC is a function of volume of the cell or formed body sensed, while RF is a function of the internal conductivity and volume of the sensed cell or formed body.

As is well known, WBC's typically have a diameter on the order of 8 to 10 microns. The non-magnetic and magnetic microspheres specifically described herein are of 0.7, 0.8, 1.78, 2.2, a combination of 2.2 and 0.8, and 3.0 micron diameters. These microsphere diameters thus clearly are "substantially smaller than the cells".

Also, although the method and the apparatus of the invention have been described utilizing whole blood samples, there can be instances where it is desired to utilize a portion of a sample with the RBC's and /or some of the WBC populations removed. Clearly, the RBC's are still removed, but arguably externally and not within the apparatus of the invention. Such removal or preparation can be carried out in numerous conventional ways, such as utilizing a lysing reagent, density or centrifugation techniques, such as ficoll, dextran, "buffycoat", etc. In an automated analyzer utilizing the invention, it would be preferable to utilize a whole blood sample for speed and integrity in the analysis of the sample.

Many modifications and variations of the present invention are possible in light of the above teachings. The samples 12, 42, 150, 180, 294, 322 and 342 can include whole blood, human body fluids containing cells, or other fluids containing formed bodies, such as bacteria, viruses and fungi. The volumes of microspheres specified are stated in weight of microspheres per volume of diluent. Although some of the examples were performed in sequential steps, the steps can also be performed simultaneously. A simultaneous analysis allows the least complex instrument module to be utilized. It is therefore, to be understood that within the scope of the appended claims, the invention may be practiced otherwise than as specifically described.

What is claimed and desired to be secured by Letters Patent of the United States is:

1. A method of obtaining at least one white blood cell population analysis from at least a portion of a whole blood sample having at least white blood cell populations therein, at least one of the white blood cell populations further having at least one subset, comprising:
    modifying the volume and/or opacity parameters of at least one white blood cell population subset of said white blood cell population of interest by binding microspheres having a monoclonal antibody bonded thereto specific to said white blood cell population subset to said white blood cell population subset, said microspheres being substantially smaller than said cells; and
    electronically analyzing said modified white blood cell population subset and said selected white blood cell population of interest with at least two electronic sensing parameters utilizing Coulter sensing techniques to determine at least one characteristic of said selected white blood cell population.

2. The method as defined in claim 1 including subtracting at least one white blood cell population from said white blood cell populations prior to analyzing said modified white blood cell population subset.

3. The method as defined in claim 2 including subtracting said white blood cell population by providing magnetic microspheres having a monoclonal antibody bonded thereto specific to said white blood cell population and mixing said magnetic microspheres with said sample to bind to said white blood cell population and removing said white blood cell population by removing at least a portion of the remainder of said sample while attracting said magnetic microspheres within a magnetic field.

4. The method as defined in claim 1 including subtracting at least the neutrophil and eosinophil populations from said white blood cell population prior to analyzing said modified white blood cell population subset.

5. The method as defined in claim 4 including subtracting said neutrophil and eosinophil populations by providing magnetic microspheres having a monoclonal antibody bonded thereto specific to said neutrophil and eosinophil populations and mixing said magnetic microspheres with said sample to bind to said neutrophil and eosinophil populations and removing said neutrophil and eosinophil populations by removing at least a portion of the remainder of said sample while attracting said magnetic microspheres within a magnetic field.

6. The method as defined in claim 1 including modifying the CD4 white blood cell population subset by providing microspheres having a specific monoclonal antibody bonded thereto which is specific to said CD4 white blood cell population subset and mixing said microspheres with said sample to bind to said CD4 subset population to shift at least one electronic characteristic of said CD4 subset population.

7. The method as defined in claim 1 including modifying the CD8 white blood cell population subset by providing microspheres having a specific monoclonal antibody bonded thereto which is specific to said CD8 white blood cell population subset and mixing said microspheres with said sample to bind to said CD8 subset population to shift at least one electronic characteristic of said CD8 subset population.

8. The method as defined in claim 1 including modifying the CD2 white blood cell population subset by providing microspheres having a specific monoclonal antibody bonded thereto which is specific to said CD2 white blood cell population subset and mixing said microspheres with said sample to bind to said CD2 subset population to shift at least one electronic characteristic of said CD2 subset population.

9. The method as defined in claim 1 including modifying the CD20 white blood cell population subset by providing microspheres having a specific monoclonal antibody bonded thereto which is specific to said CD20 white blood cell population subset and mixing said microspheres with said sample to bind to said CD20 subset population to shift at least one electronic characteristic of said CD20 subset population.

10. The method as defined in claim 1 wherein said whole blood sample includes a red blood cell population and removing the red blood cell population from said sample without significantly adversely affecting relevant qualities and/or quantities of at least one of said white blood cell populations of interest.

11. The method as defined in claim 10 wherein removal of said red blood cell population includes providing microspheres having a red blood cell specific monoclonal antibody bonded thereto and mixing said microspheres with said whole blood sample to bind to said red blood cell population; and
    removing said microspheres with said bound red blood cells from said whole blood sample.

12. The method as defined in claim 11 including providing magnetic microspheres and a magnetic field and removing said microspheres by removing said red blood cells while attracting said magnetic microspheres within said magnetic field.

13. The method as defined in claim 10 wherein removing said red blood cell population includes providing a red blood cell lyse to substantially eliminate said red blood cell population.

14. The method as defined in claim 1 including modifying the volume and/or opacity parameters of at least a second white blood cell subset of said white blood cell populations of interest by binding microspheres having a monoclonal antibody bonded thereto specific to said white blood cell population subset to said white blood cell population subset, said microspheres being substantially smaller than said cells; and electronically analyzing at least one of said modified white blood cell subset sand said selected white blood cell population of interest to determine at least one characteristic of said selected white blood cell population.

15. The method as defined in claim 14 including electronically analyzing both of said modified white blood cell subsets.

16. The method as defined in claim 14 including modifying said two white blood cell subsets by providing microspheres of a first size having a monoclonal antibody bonded thereto specific to said first white blood cell subset and providing microspheres of a second size, different from said first size, having a monoclonal antibody bonded thereto specific to said second white blood cell subset, and mixing said microspheres with said sample to bind to said white blood cell populations.

17. The method as defined in claim 1 including modifying said white blood cell population subset by providing a first set of microspheres having a monoclonal antibody bonded thereto specific to said white blood cell subset and mixing said microspheres with said sample to bind to said white blood cell populations and then providing a second set of microspheres having a monoclonal antibody bonded thereto specific to said monoclonal antibody bonded onto said first set of microspheres and mixing said second set of microspheres with said sample and said first set of microspheres to bind thereto.

18. The method as defined in claim 10 including modifying said white blood cell population subset and removing said red blood cell population substantially simultaneously.

19. The method as defined in claim 10 including modifying said white blood cell population subset and removing said red blood cell population sequentially.

20. An apparatus for obtaining at least one white blood cell population analysis from at least a portion of a whole blood sample having at least white blood cell populations therein, at least one of the white blood cell populations further having at least one subset, comprising:

means for modifying the volume and/or opacity parameters of at least one white blood cell population subset of said white blood cell population of interest by binding microspheres having a monoclonal antibody bonded thereto specific to said white blood cell population subset to said white blood cell population subset, said microspheres being substantially smaller than said cells; and means for electronically analyzing said modified white blood cell population subset and said selected white blood cell population of interest with at least two electronic sensing parameters utilizing Coulter sensing techniques to determine at least one characteristic of said selected white blood cell population.

21. The apparatus as defined in claim 20 including means for subtracting at least one white blood cell population from said white blood cell populations prior to analyzing said modified white blood cell population subset.

22. The apparatus as defined in claim 21 including means for subtracting said white blood cell population by providing magnetic microspheres having a monoclonal antibody bonded thereto specific to said white blood cell population and means for mixing said magnetic microspheres with said sample to bind to said white blood cell population and means for removing said white blood cell population by removing at least a portion of the remainder of said sample while attracting said magnetic microspheres within a magnetic field.

23. The apparatus as defined in claim 20 including means for subtracting at least the neutrophil and eosinophil populations from said white blood cell population prior to analyzing said modified white blood cell population subset.

24. The apparatus as defined in claim 23 including means for subtracting said neutrophil and eosinophil populations by providing magnetic microspheres having a monoclonal antibody bonded thereto specific to said neutrophil and eosinophil populations and means for mixing said magnetic microspheres with said sample to bind to said neutrophil and eosinophil populations and means for removing said neutrophil and eosinophil populations by removing at least a portion of the remainder of said sample while attracting said magnetic microspheres within a magnetic field.

25. The apparatus as defined in claim 20 including means for modifying the CD4 white blood cell population subset by providing microspheres having a specific monoclonal antibody bonded thereto which is specific to said CD4 white blood cell population subset and means for mixing said microspheres with said sample to bind to said CD4 subset population to shift at least one electronic characteristic of said CD4 subset population.

26. The apparatus as defined in claim 20 including means for modifying the CD8 white blood cell population subset by providing microspheres having a specific monoclonal antibody bonded thereto which is specific to said CD8 white blood cell population subset and means for mixing said microspheres with said sample to bind to said CD8 subset population to shift at least one electronic characteristic of said CD8 subset population.

27. The apparatus as defined in claim 20 including means for modifying the CD2 white blood cell population subset by providing microspheres having a specific monoclonal antibody bonded thereto which is specific to said CD2 white blood cell population subset and means for mixing said microspheres with said sample to bind to said CD2 subset population to shift at least one electronic characteristic of said CD2 subset population.

28. The apparatus as defined in claim 20 including means for modifying the CD20 white blood cell population subset by providing microspheres having a specific monoclonal antibody bonded thereto which is specific to said CD20 white blood cell population subset and means for mixing said microspheres with said sample to bind to said CD20 subset population to shift at least one electronic characteristic of said CD20 subset population.

29. The apparatus as defined in claim 20 wherein said whole blood sample includes a read blood cell population and including means for removing the red blood cell population from said sample without significantly adversely affecting relevant qualities and/or quantities of at least one of said white blood cell populations of interest.

30. The apparatus as defined in claim 29 wherein removal of said red blood cell population includes providing microspheres having a red blood cell specific monoclonal antibody bonded thereto and means for mixing said microspheres with said whole blood sample to bind to said red blood cell population; and means for removing said microspheres with said bound red blood cells from said whole blood sample 31. The apparatus as defined in claim 29 including providing magnetic microspheres and a magnetic field and means for removing said microspheres by removing said red blood cells while attracting said magnetic microspheres within said magnetic field.

32. The apparatus as defined in claim 29 wherein said means for removing said red blood cell population include providing a red blood cell lyse to substantially eliminate said red blood cell population.

33. The apparatus as defined in claim 20 including means for modifying the volume and/or opacity parameters of at least a second white blood cell subset of said white blood cell populations of interest by binding microspheres having a monoclonal antibody bonded thereto specific to said white blood cell population subset to said white blood cell population subset, said microspheres being substantially smaller than said cells; and means for electronically analyzing at last one of said modified white blood cell subsets and said selected white blood cell population of interest to determine at least one characteristic of said selected white blood cell population.

34. The apparatus as defined in claim 33 including means for electronically analyzing both of said modified white blood cell subsets.

35. The apparatus as defined in claim 33 including means for modifying said two white blood cell subsets by providing microspheres of a first size having a monoclonal antibody bonded thereto specific to said first white blood cell subset and providing microspheres of a second size, different from said first size, having a monoclonal antibody bonded thereto specific to said second white blood cell subset, and means for mixing said microspheres with said sample to bind to said white blood cell populations.

36. The apparatus as defined in claim 20 including means for modifying said white blood cell population subset by providing a first set of microspheres having a monoclonal antibody bonded thereto specific to said white blood cell subset and means for mixing said microspheres with said sample to bind to said white blood cell populations and then providing a second set of microspheres having a monoclonal antibody bonded thereto specific to said monoclonal antibody bonded onto said first set of microspheres and means for mixing said second set of microspheres with said sample and said first set of microspheres to bind thereto.

37. The apparatus as defined in claim 29 including means for modifying said white blood cell population subset and means for removing said red blood cell population substantially simultaneously.

38. The apparatus as defined in claim 29 including means for modifying said white blood cell population subset and means for removing said red blood cell population sequentially.

39. A method of obtaining at least one white blood cell population analysis from at least a portion of a whole blood sample having at least white blood cell populations therein, at least one of the white blood cell populations further having at least one subset, comprising:

modifying the volume and opacity parameters of at least one white blood cell population subset of said white blood cell population of interest by binding microspheres having a monoclonal antibody bonded thereto specific to said white blood cell population subset to said white blood cell population subset, said microspheres being substantially smaller than said cells; and electronically analyzing said modified white blood cell population subset and said selected white blood cell population of interest with at least two electronic sensing parameters utilizing Coulter sensing techniques to determine at least one characteristic of said selected white blood cell population.

40. The method as defined in claim 39 including subtracting at least one white blood cell population from said white blood cell populations prior to analyzing said modified white blood cell population subset.

41. The method as defined in claim 40 including subtracting said white blood cell population by providing magnetic microspheres having a monoclonal antibody bonded thereto specific to said white blood cell population and mixing said magnetic microspheres with said sample to bind to said white blood cell population and removing said white blood cell population by removing at least a portion of the remainder of said sample while attracting said magnetic microspheres within a magnetic field.

42. The method as defined in claim 39 including subtracting at least the neutrophil and eosinophil populations from said white blood cell population prior to analyzing said modified white blood cell population subset.

43. The method as defined in claim 42 including subtracting said neutrophil and eosinophil populations by providing magnetic microspheres having a monoclonal antibody bonded thereto specific to said neutrophil and eosinophil populations and mixing said magnetic microspheres with said sample to bind to said neutrophil and eosinophil populations and removing said neutrophil and eosinophil populations by removing at least a portion of the remainder of said sample while attracting said magnetic microspheres within a magnetic field.

44. The method as defined in claim 39 including modifying the CD4 white blood cell population subset by providing microspheres having a specific monoclonal antibody bonded thereto which is specific to said CD4 white blood cell population subset and mixing said microspheres with said sample to bind to said CD4 subset population to shift at least one electronic characteristic of said CD4 subset population.

45. The method as defined in claim 39 including modifying the CD8 white blood cell population subset by providing microspheres having a specific monoclonal antibody bonded thereto which is specific to said CD8 white blood cell population subset and mixing said microspheres with said sample to bind to said CD8 subset population to shift at least one electronic characteristic of said CD8 subset population.

46. The method as defined in claim 39 including modifying the CD2 white blood cell population subset by providing microspheres having a specific monoclonal antibody bonded thereto which is specific to said CD2 white blood cell population subset and mixing said microspheres with said sample to bind to said CD2 subset population to shift at least one electronic characteristic of said CD2 subset population.

47. The method as defined in claim 39 including modifying the CD20 white blood cell population subset by providing microspheres having a specific monoclonal antibody bonded thereto which is specific to said CD20 white blood cell population subset and mixing said microspheres with said sample to bind to said CD20 subset population to shift at least one electronic characteristic of said CD20 subset population.

48. The method as defined in claim 39 wherein said whole blood sample includes a red blood cell population and removing the red blood cell population from said sample without significantly adversely affecting relevant qualities and/or quantities of at least one of said white blood cell populations of interest.

49. The method as defined in claim 48 wherein removal of said red blood cell population includes providing microspheres having a red blood cell specific monoclonal antibody bonded thereto and mixing said microspheres with said whole blood sample to bind to said red blood cell population; and removing said microspheres with said bound red blood cells from said whole blood sample.

50. The method as defined in claim 49 including providing magnetic microspheres and a magnetic field and removing said microspheres by removing said red blood cells while attracting said magnetic microspheres within said magnetic field.

51. The method as defined in claim 48 wherein removing said red blood cell population includes providing a red blood cell lyse to substantially eliminate said red blood cell population.

52. The method as defined in claim 39 including modifying the volume and/or opacity parameters of at least a second white blood cell subset of said white blood cell populations of interest by binding microspheres having a monoclonal antibody bonded thereto specific to said white blood cell population subset to said white blood cell populations subset, said microspheres being substantially smaller than said cells; and electronically analyzing at least one of said modified white blood cell subsets and said selected white blood cell population of interest to determine at least one characteristic of said selected white blood cell population.

53. The method as defined in claim 52 including electronically analyzing both of said modified white blood cell subsets.

54. The method as defined in claim 52 including modifying said two white blood cell subsets by providing microspheres of a first size having a monoclonal antibody bonded thereto specific to said first white blood cell subset and providing microspheres of a second size, different from said first size, having a monoclonal antibody bonded thereto specific to said second white blood cell subset, and mixing said microspheres with said sample to bind to said white blood cell populations.

55. The method as defined in claim 39 including modifying said white blood cell population subset by providing a first set of microspheres having a monoclonal antibody bonded thereto specific to said white blood cell subset and mixing said microspheres with said sample to bind to said white blood cell populations and then providing a second set of microspheres having a monoclonal antibody bonded thereto specific to said monoclonal antibody bonded onto said first set of microspheres and mixing said second set of microspheres with said sample and said first set of microspheres to bind thereto.

56. The method as defined in claim 48 including modifying said white blood cell population subset and removing said red blood cell population substantially simultaneously.

57. The method as defined in claim 48 including modifying said white blood cell population subset and removing said red blood cell population sequentially.

58. An apparatus for obtaining at least one white blood cell population analysis from at least a portion of a whole blood sample having at least white blood cell populations therein, at least one of the white blood cell populations further having at least one subset, comprising:

means for modifying the volume and opacity parameters of at last one white blood cell population subset of said white blood cell population of interest by binding microspheres having a monoclonal antibody bonded thereto specific to said white blood cell population subset to said white blood cell population subset, said microspheres being substantially smaller than said cells; and means for electronically analyzing said modified white blood cell population subset and said selected white blood cell population of interest with at least two electronic sensing parameters utilizing Coulter sensing techniques to determine at least one characteristic of said selected white blood cell population.

59. The apparatus as defined in claim 58 including means for subtracting at least one white blood cell population from said white blood cell poulations prior to analyzing said modified white blood cell population subset.

60. The apparatus as defined in claim 59 including means for subtracting said white blood cell population by providing magnetic microspheres having a monoclonal antibody bonded thereto specific to said white blood cell population and means for mixing said magnetic microspheres with said sample to bind to said white blood cell population and means for removing said white blood cell population by removing at least a portion of the remainder of said sample while attracting said magnetic microspheres within a magnetic field.

61. The apparatus as defined in claim 58 including means for subtracting at least the neutrophil and eosinophil populations from said white blood cell population prior to analyzing said modified white blood cell population subset.

62. The apparatus as defined in claim 61 including means for subtracting said neutrophil and eosinophil populations by providing magnetic microspheres having a monoclonal antibody bonded thereto specific to said neutrophil and eosinophil populations and means for mixing said magnetic microspheres with said sample to bind to said neutrophil and eosinophil populations and removing said neutrophil and eosinophil populations by removing at least a portion of the remainder of said sample while attracting said magnetic microspheres within a magnetic field.

63. The apparatus as defined in claim 58 including means for modifying the CD4 white blood cell population subset by providing microspheres having a specific monoclonal antibody bonded thereto which is specific to said CD4 white blood cell population subset and means for mixing said microspheres with said sample to bind to said CD4 subset population to shift at least one electronic characteristic of said CD4 subset population.

64. The apparatus as defined in claim 58 including means for modifying the CD8 white blood cell population subset by providing microspheres having a specific monoclonal antibody bonded thereto which is specific to said CD8 white blood cell population subset and means for mixing said microspheres with said sample to bind to said CD8 subset population to shift at least one electronic characteristic of said CD8 subset population.

65. The apparatus as defined in claim 58 including means for modifying the CD2 white blood cell population subset by providing microspheres having a specific monoclonal antibody bonded thereto which is specific to said CD2 white blood cell population subset and means for mixing said microspheres with said sample to bind to said CD2 subset population to shift at least one electronic characteristic of said CD2 subset population.

66. The apparatus as defined in claim 58 including means for modifying the CD20 white blood cell population subset by providing microspheres having a specific monoclonal antibody bonded thereto which is specific to said CD20 white blood cell population subset and means for mixing said microspheres with said sample to bind to said CD20 subset population to shift at least one electronic characteristic of said CD20 subset population.

67. The apparatus as defined in claim 58 wherein said whole blood sample includes a red blood cell population and including means for removing the red blood cell population from said sample without significantly adversely affecting relevant qualities and/or quantities of at least one of said white blood cell populations of interest.

68. The apparatus as defined in claim 67 wherein removal of said red blood cell population includes providing microspheres having a red blood cell specific monoclonal antibody bonded thereto and means for mixing said microspheres with said whole blood sample to bind to said red blood cell population; and
    means for removing said microspheres with said bound red blood cells from said whole blood sample.

69. The apparatus as defined in claim 68 including providing magnetic microspheres and a magnetic field and means for removing said microspheres by removing said red blood cells while attracting said magnetic microspheres within said magnetic field.

70. The apparatus as defined in claim 67 wherein said means for removing said red blood cell population include providing red blood cell lyse to substantially eliminate said red blood cell population.

71. The apparatus as defined in claim 58 including means for modifying the volume and/or opacity parameters of at least a second white blood cell subset of said white blood cell populations of interest by binding microspheres having a monoclonal antibody bonded thereto specific to said white blood cell population subset to said white blood cell population subset, said microspheres being substantially smaller than said cells; and
    means for electronically analyzing at least one of said modified white blood cell subsets and said selected white blood cell population of interest to determine at least one characteristic of said selected white blood cell population.

72. The apparatus as defined in claim 71 including means for electronically analyzing both of said modified white blood cell subsets.

73. The apparatus as defined in claim 71 including means for modifying said two white blood cell subsets by providing microspheres of a first size having a monoclonal antibody bonded thereto specific to said first white blood cell subset and providing microspheres of a second size, different from said first size, having a monoclonal antibody bonded thereto specific to said second white blood cell subset, and means for mixing said microspheres with said sample to bind to said white blood cell populations.

74. The apparatus as defined in claim 58 including means for modifying said white blood cell population subset by providing a first set of microspheres having a monoclonal antibody bonded thereto specific to said white blood cell subset and means for means for mixing said microspheres with said sample to bind to said white blood cell populations and then providing a second set of microspheres having a monoclonal antibody bonded thereto specific to said monoclonal antibody bonded onto said first set of microspheres and mixing said second set of microspheres with said sample and said first set of microspheres to bind thereto.

75. The apparatus as defined in claim 67 including means for modifying said white blood cell population subset and means for removing said red blood cell population substantially simultaneously.

76. The apparatus as defined in claim 67 including means for modifying said white blood cell population subset and means for removing said red blood cell population sequentially.

77. A method of obtaining a multi-part white blood cell population differential from at least a portion of a whole blood sample having at least white blood cell populations therein, comprising:
    electronically counting at least said white blood cell populations of granulocytes, monocytes and lymphocytes with at least two electronic sensing parameters utilizing Coulter sensing techniques;
    subtracting the neutrophil population contribution from said white blood cell populations by binding microspheres having a monoclonal antibody bonded thereto specific to said neutrophil population to said neutrophil population;
    electronically counting at least said remaining white blood cell populations of monocytes, lymphocytes, eosinophils and basophils with at least two electronic sensing parameters utilizing Coulter sensing techniques; and
    comparing said two counts to obtain a count of said white blood cell population of neutrophils and thereby obtaining at least a five-part white blood cell differential.

78. The method as defined in claim 77 wherein said whole blood sample includes a red blood cell population and removing said red blood cell population from said sample without adversely affecting relevant qualities and/or quantities of said white blood cell populations.

79. The method as defined in claim 78 wherein removal of said red blood cell population includes providing microspheres having a red blood cell specific monoclonal antibody bonded thereto and mixing said microspheres with said whole blood sample to bind to said red blood cell population; and removing said microspheres with said bound red blood cells from said whole blood sample.

80. The method as defined in claim 79 including providing magnetic microspheres and a magnetic field and removing said microspheres by removing said red blood cells while attracting said magnetic microspheres within said magnetic field.

81. The method as defined in claim 79 including rapidly mixing said microspheres with said whole blood sample to bind said red blood cell population to said microspheres in less than sixty seconds.

82. The method as defined in claim 78 wherein removing said red blood cell population includes providing microspheres having a red blood cell specific monoclonal antibody bonded thereto and mixing said microspheres with said whole blood sample to bind to said red blood cell population and providing a red blood cell lyse with said microspheres to eliminate a portion of said red blood cell populations to decrease the number of microspheres necessary to remove said red blood cell populations; and removing said microspheres with said red blood cells bound thereto from said whole blood sample.

83. The method as defined in claim 82 including providing magnetic microspheres and a magnetic field and removing said microspheres by removing said red blood cells while attracting said magnetic microspheres within said magnetic field.

84. The method as defined in claim 82 including rapidly mixing said microspheres with said whole blood sample to bind said red blood cell population to said microspheres in less than sixty seconds and to provide and lysing action.

85. The method as defined in claim 78 wherein removing said red blood cell population includes providing a red blood cell lyse to substantially eliminate said red blood cell population.

86. The method as defined in claim 77 wherein subtracting the neutrophil population includes providing microspheres having a neutrophil specific monoclonal antibody bonded thereto and mixing said microspheres with said sample to bind to said neutrophil population to shift at least one electronic characteristic of said neutrophil population.

87. The method as defined in claim 77 wherein subtracting the neutrophil populations includes providing microspheres having a neutrophil specific monoclonal antibody bonded thereto and mixing said microspheres with said sample to bind to said neutrophil population; and removing said microspheres with said neutrophil population bound thereto from said sample.

88. The method as defined in claim 87 including providing magnetic microspheres and a magnetic field and removing said microspheres by removing said neutrophil population while attracting magnetic microspheres within said magnetic field.

89. The method as defined in claim 87 including rapidly mixing said microspheres with said sample to bind said neutrophil population to said microspheres in less than sixty seconds.

90. An apparatus for obtaining a multi-part white blood cell population differential from at least a portion of a whole blood sample having at least white blood cell populations therein, comprising:

means for electronically counting at least said white blood cell populations of granulocytes, monocytes and lymphoytes with at least two electronic sensing parameters utilizing Coulter sensing techniques;

means for subtracting the neutrophil population contribution from said white blood cell populations by binding microspheres having a monoclonal antibody bonded thereto specific to said neutrophil population to said neutrophil population;

means for electronically counting at least said remaining white blood cell populations of monocytes, lymphocytes, eosinophils and basophils with at least two electronic sensing parameters utilizing Coulter sensing techniques; and means for comparing said two counts to obtain a count of said white blood cell population of neutrophils and thereby obtaining at least a five-part white blood cell differential.

91. The apparatus as defined in claim 90 wherein said whole blood sample includes a red blood cell population and means for removing said red blood cell population from said sample without adversely affecting relevant qualities and/or quantities of said white blood cell populations.

92. The apparatus as defined in claim 91 wherein removal of said red blood cell population includes providing microspheres having a red blood cell specific monoclonal antibody bonded thereto and means for mixing said microspheres with said whole blood sample to bind to said red blood cell population; and means for removing said microspheres with said bound red blood cells from said whole blood sample.

93. The apparatus as defined in claim 92 including providing magnetic microspheres and a magnetic field and removing said microspheres by removing said red blood cells while attracting said magnetic microspheres within said magnetic field.

94. The apparatus as defined in claim 92 including means for rapidly mixing said microspheres with said whole blood sample to bind said red blood cell population to said microspheres in less than sixty seconds.

95. The apparatus as defined in claim 91 wherein said means for removing said red blood cell population include providing microspheres having a red blood cell specific monoclonal antibody bonded thereto and means for mixing said microspheres with said whole blood sample to bind to said red blood cell population and providing a red blood cell lyse with said microspheres to eliminate a portion of said red blood cell populations to decrease the number of microspheres necessary to remove said red blood cell populations; and means for removing said microspheres with said red blood cells bound thereto from said whole blood sample.

96. The apparatus as defined in claim 95 including providing magnetic microspheres and a magnetic field and removing said microspheres by removing said red blood cells while attracting said magnetic microspheres within said magnetic field.

97. The apparatus as defined in claim 95 including means for rapidly mixing said microspheres with said whole blood sample to bind said red blood cell population to said microspheres in less than sixty seconds and to provide said lysing action.

98. The apparatus as defined in claim 91 wherein said means for removing said red blood cell population includes providing a red blood cell lyse to substantially eliminate said red blood cell population.

99. The apparatus as defined in claim 90 wherein said means for subtracting the neutrophil population include providing microspheres having a neutrophil specific monoclonal antibody bonded thereto and means for mixing said microspheres with said sample to bind to said neutrophil population to shift at least one electronic characteristic of said neutrophil population.

100. The apparatus as defined in claim 90 wherein said means for subtracting the neutrophil populations include providing microspheres having a neutrophil specific monoclonal antibody bonded thereto and means for mixing said microspheres with said sample to bind to said neutrophil population; and means for removing said microspheres with said neutrophil population bound thereto from said sample.

101. The apparatus as defined in claim 100 including providing magnetic microspheres and a magnetic field and removing said microspheres by removing said neutrophil population while attracting said magnetic microspheres within said magnetic field.

102. The apparatus as defined in claim 100 including means for rapidly mixing said microspheres with said sample to bind said neutrophil population to said microspheres in less than sixty seconds.

103. A method of obtaining a multi-part white blood cell population differential from at least a portion of a whole blood sample having at least white blood cell populations therein, comprising:

electronically counting at least said white blood cell populations of granulocytes, monocytes and lymphocytes in a first portion of said sample with at least two electronic sensing parameters utilizing Coulter sensing techniques;

subtracting the neutrophil population contribution from said white blood cell populations by binding microspheres having a monoclonal antibody bonded thereto specific to said neutrophil population to said neutrophil population from a second portion of said sample without adversely affecting the relevant qualities and/or quantities of said remaining white blood cell populations;

electronically counting at least said remaining white blood cell populations of monocytes, lymphocytes, eosinophils and basophils in said second portion with at least two electronic sensing parameters utilizing Coulter sensing techniques; and comparing said two counts from said first and second portions to obtain a count of said white blood cell populations of neutrophils and thereby obtaining at least a five-part white blood cell differential.

104. The method as defined in claim 103 wherein said whole blood sample includes a red blood cell population and removing said red blood cell population from said sample without adversely affecting relevant qualities and/or quantities of said white blood cell populations prior to the counting of said first portion and also removing said red blood cell population from said second portion prior to the counting thereof.

105. The method as defined in claim 104 wherein removing said red blood cell population from at least one of said portions includes providing microspheres having a red blood cell specific monoclonal antibody bonded thereto and mixing said microspheres with said whole blood sample to bind to said red blood cell population; and removing said microspheres with said red blood cells bound thereto from said whole blood sample.

106. The method as defined in claim 105 including providing magnetic microspheres and a magnetic field and removing said microspheres by removing said red blood cells while attracting said magnetic microspheres within said magnetic field.

107. The method as defined in claim 105 including rapidly mixing said microspheres with said whole blood sample to bind said red blood cell population to said microspheres in less than sixty seconds.

108. The method as defined in claim 104 wherein removing said red blood cell population from at least one of said portions includes providing microspheres having a red blood cell specific monoclonal antibody bonded thereto and mixing said microspheres with said whole blood sample to bind to said red blood cell population and providing a red blood cell lyse with said microspheres to eliminate a portion of said red blood cell populations to decrease the number of microspheres necessary to remove said red blood cell populations; and removing said microspheres with said red blood cells bound thereto from said whole blood sample.

109. The method as defined in claim 108 including providing magnetic microspheres and a magnetic field and removing said microspheres by removing said red blood cells while attracting said magnetic microspheres within said magnetic field.

110. The method as defined in claim 108 including rapidly mixing said microspheres with said whole blood sample portion to bind said red blood cell population to said microspheres in less than sixty seconds and to provide said lysing action.

111. The method as defined in claim 104 wherein removing said red blood cell population from at least one of said portions includes providing a red blood cell lyse to substantially eliminate said red blood cell population.

112. The method as defined in claim 103 wherein subtracting the neutrophil population in said second portion includes providing microspheres having a neutrophil specific monoclonal antibody bonded thereto and mixing said microspheres with said whole blood sample to bind to said neutrophil population to shift at least one electronic characteristic of said neutrophil population.

113. The method as defined in claim 103 wherein subtracting the neutrophil population in said second portion includes providing microspheres having a neutrophil specific monoclonal antibody bonded thereto and mixing said microspheres with said whole blood sample to bind to said neutrophil population; and removing said microspheres with said neutrophil population bound thereto from said sample.

114. The method as defined in claim 113 including providing magnetic microspheres and a magnetic field and removing said microspheres by removing said neutrophil population while attracting said magnetic microspheres within said magnetic field.

115. The method as defined in claim 113 including rapidly mixing said microspheres with said whole blood sample to bind said neutrophil population to said microspheres in less than sixty seconds.

116. An apparatus for obtaining a multi-part white blood cell population differential from at least a portion of a whole blood sample having at least white blood cell populations therein, comprising:
- means for electronically counting at least said white blood cell populations of granulocytes, monocytes and lymphocytes in a first portion of said sample with at least two electronic sensing parameters utilizing Coulter sensing techniques;
- means for subtracting the neutrophil population contribution from said white blood cell populations by binding microspheres having a monoclonal antibody bonded thereto specific to said neutrophil population to said neutrophil population from a second portion of said sample without adversely affecting the relevant qualities and/or quantities of said remaining white blood cell populations;
- means for electronically counting at least said remaining white blood cell populations of monocytes, lymphocytes, eosinophils and basophils in said second portion with at least two electronic sensing parameters utilizing Coulter sensing techniques; and
- means for comparing said two counts from said first and second portions to obtain a count of said white blood cell populations of neutrophils and thereby obtaining at least a five-part white blood cell differential.

117. The apparatus as defined in claim 116 wherein said whole blood sample includes a red blood cell population and including means for removing said red blood cell population from said sample without adversely affecting relevant qualities and/or quantities of said white blood cell populations prior to the counting of said first portion and also removing said red blood cell population from said second portion prior to the coating thereof.

118. The apparatus as defined in claim 112 wherein said means for removing said red blood cell population from at least one of said portions include providing microspheres having a red blood cell specific monoclonal antibody bonded thereto and means for mixing said microspheres with said whole blood sample to bind to said red blood cell population; and
- means for removing said microspheres with said red blood cells bound thereto from said whole blood sample.

119. The apparatus as defined in claim 118 including providing magnetic microspheres an a magnetic field and removing said microspheres by removing said red blood cells while attracting said magnetic microspheres within said magnetic field.

120. The apparatus as defined in claim 118 including means for rapidly mixing said microspheres with said whole blood sample to bind said red blood cell population to said microspheres in less than sixty seconds.

121. The apparatus as defined in claim 117 wherein said means for removing said red blood cell population from at least one of said portions include providing microspheres having a red blood cell specific monoclonal antibody bonded thereto and means for mixing said microspheres with said whole blood sample to bind to said red blood cell population and providing a red blood cell lyse with said microspheres to eliminate a portion of said red blood cell populations to decrease the number of microspheres necessary to remove said red blood cell populations; and
- means for removing said microspheres with said red blood cells bound thereto from said whole blood sample.

122. The apparatus as defined in claim 121 including providing magnetic microspheres and a magnetic field and removing said microspheres by removing said red blood cells while attracting said magnetic microspheres within said magnetic field.

123. The apparatus as defined in claim 121 including means for rapidly mixing said microspheres with said whole blood sample portion to red blood cell population to said microspheres in less than sixty seconds and to provide said lysing action.

124. The apparatus as defined in claim 117 wherein said means for removing said red blood cell population from at least one of said portions include providing a red blood cell lyse to substantially eliminate said red blood cell population.

125. The apparatus as defined in claim 116 wherein said means for subtracting the neutrophil population in said second portion include providing microspheres having a neutrophil specific monoclonal antibody bonded thereto and means for mixing said microspheres with said whole blood sample to bind to said neutrophil population to shift at least one electronic characteristic of said neutrophil population.

126. The apparatus as defined in claim 118 wherein said means for subtracting the neutrophil population in said second portion include providing microspheres having a neutrophil specific monoclonal antibody bonded thereto and means for mixing said microspheres with said whole blood sample to bind to said neutrophil population; and
- means for removing said microspheres with said neutrophil population bound thereto from said sample.

127. The apparatus as defined in claim 126 including providing magnetic microspheres and a magnetic field and removing said microspheres by removing said neutrophil population while attracting said magnetic microspheres within said magnetic field.

128. The apparatus as defined in claim 126 including means for rapidly mixing said microspheres with said whole blood sample to bind said neutrophil population to said microspheres in less than sixty seconds.

129. A method of obtaining a multi-part white blood cell population differential from at least a portion of a whole blood sample having at least white blood cell populations therein, comprising:
- shifting the neutrophil population characteristic contribution with respect to the other white blood cell populations by binding microspheres having monoclonal antibody bonded thereto specific to said neutrophil population to said neutrophil population, said microspheres being substantially smaller than said neutrophil population cells; and
- electronically counting at least said white blood cell populations of monocytes, lymphocytes, neutrophils, eosinophils and basophils with at least two electronic sensing parameters utilizing Coulter sensing techniques and thereby obtaining at least a five-part white blood cell differential.

130. The method as defined in claim 129 wherein said whole blood sample includes a red blood cell population and removing said red blood cell population from said sample without adversely affecting relevant qualities and/or quantities of said white blood cell populations.

131. The method as defined in claim 130 wherein removing said red blood cell population includes providing microspheres having a red blood cell specific monoclonal antibody bonded thereto and mixing said microspheres with said whole blood sample to bind to said red blood cell population; and removing said microspheres with said red blood cells bound thereto from said whole blood sample.

132. The method as defined in claim 131 including providing magnetic microspheres and a magnetic field and removing said microspheres by removing said red blood cells while attracting said magnetic microspheres with said magnetic field.

133. The method as defined in claim 131 including rapidly mixing said microspheres with said whole blood sample to bind said red blood cell population to said microspheres in less than sixty seconds.

134. The method as defined in claim 130 wherein removing said red blood cell population includes providing microspheres having a red blood cell specific monoclonal antibody bonded thereto and mixing said microspheres with said whole blood sample to bind to said red blood cell population and providing a red blood cell lyse with said microspheres to eliminate a portion of said red blood cell populations to decrease the number of microspheres necessary to remove said red blood cell population; and removing said microspheres with said red blood cells bound thereto from said whole blood sample.

135. The method as defined in claim 134 including providing magnetic microspheres and a magnetic field and removing said microspheres by removing said red blood cells while attracting said magnetic microspheres within said magnetic field.

136. The method as defined in claim 134 including rapidly mixing said microspheres with said whole blood sample to bind said red blood cell population to said microspheres in less than sixty seconds and to provide said lysing action.

137. The method as defined in claim 130 wherein removing said red blood cell population includes providing a red blood cell lyse to substantially eliminate said red blood cell population.

138. The method as defined in claim 129 wherein shifting the neutrophil population includes providing microspheres having a neutrophil specific monoclonal antibody bonded thereto and mixing said microspheres with said sample to bind to said neutrophil population to shift at least one electronic characteristic of said neutrophil population.

139. The method as defined in claim 138 including rapidly mixing said microspheres with said sample to bind said neutrophil population to said microspheres in less than sixty seconds.

140. An apparatus for obtaining a multi-part white blood cell population differential from at least a portion of a whole blood sample having at least white blood cell populations therein, comprising:

means for shifting the neutrophil population characteristic contribution with respect to the other white blood cell populations by binding microspheres having a monoclonal antibody bonded thereto specific to said neutrophil population to said neutrophil population, said microspheres being substantially smaller than said neutrophil population cells; and means for electronically counting at least said white blood cell populations of monocytes, lymphocytes, neutrophils, eosinophils and basophils with at least two electronic sensing parameters utilizing Coulter sensing techniques and thereby obtaining at least a five-part white blood cell differential.

141. The apparatus as defined in claim 140 wherein said whole blood sample includes a red blood cell population and means for removing said red blood cell population from said sample without adversely affecting relevant quantities and/or quantities of said white blood cell populations.

142. The apparatus as defined in claim 141 wherein said means for removing said red blood cell population include providing microspheres having a red blood cell specific monoclonal antibody bonded thereto and means for mixing said microspheres with said whole blood sample to bind to said red blood cell population; and means for removing said microspheres with said red blood cells bound thereto from said whole blood sample.

143. The apparatus as defined in claim 142 including providing magnetic microspheres and a magnetic field and removing said microspheres by removing said red blood cells while attracting said magnetic microspheres within said magnetic field.

144. The apparatus as defined in claim 142 including means for rapidly mixing said microspheres with said whole blood sample to bind said red blood cell population to said microspheres in less than sixty seconds.

145. The apparatus as defined in claim 141 wherein said means for removing said red blood cell population include providing microspheres having a red blood cell specific monoclonal antibody bonded thereto and means for mixing said microspheres with said whole blood sample to bind to said red blood cell population and providing a red blood cell lyse with said microspheres to eliminate a portion of said red blood cell populations to decrease the number of microspheres necessary to remove said red blood cell population; and means for removing said microspheres with said red blood cells bound thereto from said whole blood sample.

146. The apparatus as defined in claim 145 including providing magnetic microspheres and a magnetic field and removing said microspheres by removing said red blood cells while attracting said magnetic microspheres within said magnetic field.

147. The apparatus as defined in claim 145 including means for rapidly mixing said microspheres with said whole blood sample to bind said red blood cell population to said microspheres in less than sixty seconds and to provide said lysing action.

148. The apparatus as defined in claim 141 wherein said means for removing said red blood cell population include providing a red blood cell lyse to substantially eliminate said red blood cell population.

149. The apparatus as defined in claim 140 wherein said mans for shifting the neutrophil population include providing microspheres having a neutrophil specific monoclonal antibody bonded thereto and mans for mixing said microspheres with said sample to bind to said neutrophil population to shift at least one electronic characteristic of said neutrophil population.

150. The apparatus as defined in claim 149 including means for rapidly mixing said microspheres with said sample to bind said neutrophil population to said microspheres in less than sixty seconds.

151. A method of obtaining at least one white blood cell population analysis from at least a portion of a whole blood sample having at least white blood cell populations therein, at least one of said white blood cell populations further having at least two subsets, comprising:
- subtracting at least one subset contribution from its specific white blood cell population by binding microspheres having a monoclonal antibody bonded thereto specific to said white blood cell population subset to said white blood cell population subset, said microspheres being substantially smaller than said cells; and
- electronically analyzing said subtracted white blood cell population with at least two electronic sensing parameters utilizing Coulter sensing techniques subset and said selected white blood cell population to determine at least one characteristic of said selected white blood cell population.

152. The method as defined in claim 151 wherein said whole blood sample includes a red blood cell population and removing said red blood cell population from said sample without adversely affecting relevant quantities and/or quantities of said white blood cell populations.

153. An apparatus for obtaining at least one white blood cell population analysis from at least a portion of a whole blood sample having at least white blood cell populations therein, at least one of said white blood cell populations further having at least two subsets, comprising:
- means for subtracting at least one subset contribution from its specific white blood cell population by binding microspheres having a monoclonal antibody bonded thereto specific to said white blood cell population subset to said white blood cell population subset, said microspheres being substantially smaller than said cells; and
- means for electronically analyzing said subtracted white blood cell population with at least two electronic sensing parameters utilizing Coulter sensing techniques subset and said selected white blood cell population to determine at least one characteristic of said selected white blood cell population.

154. The apparatus as defined in claim 153 wherein said whole blood sample includes a red blood cell population and means for removing said red blood cell population from said sample without adversely affecting relevant quantities and/or quantities of said white blood cell populations.

155. A method of obtaining a classification of a sample of cells or formed bodies, comprising:
- modifying the volume and/or opacity parameters of at least one population of the cells or formed bodies of interest by binding microspheres having a monoclonal antibody bonded thereto specific to cells or formed bodies to cells or formed bodies, said microspheres being substantially smaller than said cells or said formed bodies; and
- electronically analyzing said modified cells or formed bodies of interest and the remaining cells or formed bodies with at least two electronic sensing parameters utilizing Coulter sensing techniques to determine at least one characteristic of said cells or formed bodies of interest.

156. The method as defined in claim 155 including modifying the volume and opacity parameters of at least one population of the cells of interest.

157. The method as defined in claim 155 including modifying the volume and opacity parameters of at least one population of the formed bodies of interest.

158. An apparatus for obtaining a classification of a sample of cells or formed bodies, comprising:
- means for modifying the volume and/or opacity parameters of at least one population of the cells or formed bodies of interest by binding microspheres having a monoclonal antibody bonded thereto specific to cells or formed bodies to cells or formed bodies, said microspheres being substantially smaller than said cells or formed bodies; and
- means for electronically analyzing said modified cells or formed bodies of interest and the remaining cells or formed bodies with at least two electronic sensing parameters utilizing Coulter sensing techniques to determine at least one characteristic of said cells or formed bodies of interest.

159. The apparatus as defined in claim 158 including means for modifying the volume and opacity parameters of at least one population of the cells of interest.

160. The apparatus as defined in claim 158 including means for modifying the volume and opacity parameters of at least one population of the formed bodies of interest.

* * * * *